(12) United States Patent
Mistretta et al.

(10) Patent No.: US 10,433,797 B2
(45) Date of Patent: *Oct. 8, 2019

(54) SYSTEMS AND METHODS FOR ULTRA LOW DOSE CT FLUOROSCOPY

(71) Applicant: Wisconsin Alumni Research Foundation, Madison, WI (US)

(72) Inventors: Charles A. Mistretta, Madison, WI (US); Fred T. Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/936,039

(22) Filed: Mar. 26, 2018

(65) Prior Publication Data

US 2019/0076103 A1    Mar. 14, 2019

Related U.S. Application Data

(63) Continuation of application No. 15/831,051, filed on Dec. 4, 2017.

(Continued)

(51) Int. Cl.
*A61B 6/03* (2006.01)
*A61B 6/00* (2006.01)
(Continued)

(52) U.S. Cl.
CPC ............. *A61B 6/032* (2013.01); *A61B 6/022* (2013.01); *A61B 6/4057* (2013.01); *A61B 6/466* (2013.01);
(Continued)

(58) Field of Classification Search
CPC ......... A61B 6/032; A61B 34/20; A61B 6/022; A61B 6/4057; A61B 6/466; A61B 6/469;
(Continued)

(56) References Cited

U.S. PATENT DOCUMENTS 5,068,882 A * 11/1991 Eberhard ............... A61B 6/032
378/11
5,841,830 A * 11/1998 Barni ..................... A61B 6/032
378/15

(Continued)

FOREIGN PATENT DOCUMENTS

WO    WO-2017/025842 A1    2/2017

OTHER PUBLICATIONS

Kornowski et al., Fractional Flow Reserve Derived From Routine Coronary Angiograms, Journal of the American College of Cardiology, vol. 68, Issue 20, Nov. 15-22, 2016, 3 pages.
(Continued)

*Primary Examiner* — Thomas J Hong
*Assistant Examiner* — Helene Bor
(74) *Attorney, Agent, or Firm* — Foley & Lardner LLP

(57) ABSTRACT

According to at least one aspect, a method for computed tomography (CT) fluoroscopy can include acquiring a plurality of pairs of projections of an interventional device using CT fluoroscopy. Each pair of the projections can be obtained at a predetermined first angular separation greater than a second angular separation used for a full dose CT scan of a target object, by rotating a gantry of a CT scanner. The method can include identifying a position of the interventional device in real time for each pair of the projections, using back-projection of images of the interventional device from the respective pair of projections. The method can include superimposing an image of the interventional device on a 3-D image of an anatomical region at an identified position of the interventional device.

24 Claims, 11 Drawing Sheets

Related U.S. Application Data

(60) Provisional application No. 62/558,218, filed on Sep. 13, 2017.

(51) Int. Cl.

| | | |
|---|---|---|
| *A61M 27/00* | (2006.01) | |
| *A61M 25/09* | (2006.01) | |
| *A61F 2/95* | (2013.01) | |
| *A61B 17/88* | (2006.01) | |
| *A61B 17/34* | (2006.01) | |
| *A61B 17/29* | (2006.01) | |
| *A61B 6/02* | (2006.01) | |
| *A61B 34/20* | (2016.01) | |
| *A61B 90/00* | (2016.01) | |
| *A61M 25/01* | (2006.01) | |
| *A61M 29/02* | (2006.01) | |
| *A61B 90/11* | (2016.01) | |

(52) U.S. Cl.
CPC .............. *A61B 6/469* (2013.01); *A61B 6/504* (2013.01); *A61B 6/5223* (2013.01); *A61B 6/5235* (2013.01); *A61B 6/5264* (2013.01); *A61B 6/542* (2013.01); *A61B 17/29* (2013.01); *A61B 17/3403* (2013.01); *A61B 17/8872* (2013.01); *A61B 34/20* (2016.02); *A61F 2/95* (2013.01); *A61M 25/09* (2013.01); *A61M 27/002* (2013.01); *A61B 90/11* (2016.02); *A61B 2034/2065* (2016.02); *A61B 2090/363* (2016.02); *A61B 2090/3762* (2016.02); *A61M 2025/0166* (2013.01); *A61M 2029/025* (2013.01)

(58) Field of Classification Search
CPC ..... A61B 6/504; A61B 6/5223; A61B 6/5235; A61B 6/5264; A61B 6/542; A61B 17/29
See application file for complete search history.

(56) References Cited

U.S. PATENT DOCUMENTS

| | | | |
|---|---|---|---|
| 6,149,592 A * | 11/2000 | Yanof | A61B 90/36 600/427 |
| 9,414,799 B2 | 8/2016 | Mistretta et al. | |
| 2005/0207529 A1 | 9/2005 | Boese et al. | |
| 2006/0120581 A1 * | 6/2006 | Eck | A61B 6/481 382/128 |
| 2011/0286646 A1 * | 11/2011 | Chen | G06T 11/006 382/131 |
| 2012/0243655 A1 | 9/2012 | Ninomiya et al. | |
| 2013/0044856 A1 | 2/2013 | Gotman et al. | |
| 2013/0089252 A1 * | 4/2013 | Shechter | G06T 5/002 382/131 |
| 2013/0202079 A1 * | 8/2013 | Yu | A61B 6/5258 378/19 |
| 2016/0282432 A1 | 9/2016 | Wang | |
| 2016/0371862 A1 | 12/2016 | Silver et al. | |

OTHER PUBLICATIONS

Yao et al., Image-Based Fractional Flow Reserve Using Coronary Angiography, IEEE Nuclear Science Symposium and Medical Imaging Conference (2013 NSS/MIC), 2013, 4 pages.

Chen et al., Synchronized multiartifact reduction with tomographic reconstruction (SMART-RECON): A statistical model based iterative image reconstruction method to eliminate limited-view artifacts and to mitigate the temporal-average artifacts in time-resolved CT, Medical Physics 42 (8), Aug. 2015, 10 pages.

Lauzier et al., Noise spatial nonuniformity and the impact of statistical image reconstruction in CT myocardial perfusion imaging, Medical Physics 39 (7), Jul. 2012, 14 pages.

Li et al., Statistical Image Reconstruction via Denoised Ordered-Subset Statistically Penalized Algebraic Reconstruction Technique (DOS-SPART), Conference Paper in Proceedings of SPIE—The International Society for Optical Engineering, Mar. 2014, 8 pages.

Li et al., Statistical Model Based Iterative Reconstruction in myocardial CT perfusion: Exploitation of the Low Dimensionality of the Spatial-Temporal Image Matrix, Poster, dated Mar. 2015, 1 page.

Tao et al., Low dose dynamic CT myocardial perfusion imaging using a statistical iterative reconstruction method, Medical Physics 41 (7), Jul. 2014, 14 pages.

International Search Report and Written Opinion for International Application No. PCT/US2018/049780, dated Dec. 31, 2018, 9 pages.

* cited by examiner

SYSTEMS AND METHODS FOR ULTRA LOW DOSE CT FLUOROSCOPY

CROSS-REFERENCE TO RELATED APPLICATIONS

This application is a continuation of U.S. application Ser. No. 15/831,051, filed Dec. 4, 2017, which claims the benefit of and priority to U.S. Provisional Application No. 62/558,218, filed Sep. 13, 2017, both of which are hereby incorporated by reference herein in their entireties.

BACKGROUND OF THE DISCLOSURE

The present disclosure relates generally to the field of computed tomography (CT), including but not limited to methods and systems for ultra-low dose CT fluoroscopy.

CT fluoroscopy is an invaluable tool for use during CT-guided interventions such as biopsy, drainage, and ablations. In many centers, CT-fluoroscopy is the dominant modality used to guide non-vascular interventions in the chest, abdomen, pelvis, and musculoskeletal system. Most modern CT scanners are capable of performing CT fluoroscopic imaging procedures. For instance, a CT scanner can be programmed to perform CT fluoroscopy data acquisition. There are likely several hundred thousand related procedures performed in the United States per annum, and potentially millions worldwide.

SUMMARY OF THE DISCLOSURE

According to at least one aspect, a method for computed tomography (CT) fluoroscopy can include acquiring a plurality of pairs of projections of an interventional device for a target object using CT fluoroscopy, by rotating a gantry of a CT scanner. Each pair of the projections can be obtained at a predetermined first angular separation that is greater than a second angular separation used for a full dose CT scan of a target object. The full dose CT scan can have a number of acquired projections per gantry rotation being at least two times higher than that from the acquisition of the pairs projections of the interventional device. The method can include identifying a position of the interventional device in real time for each pair of the projections, using back-projection of images of the interventional device from the respective pair of projections. The method can include forming at least one two dimensional (2-D) or three dimensional (3-D) image of the interventional device using the plurality of pairs of projections and the identified positions of the interventional device. The method can include superimposing the at least one 2-D or 3-D image of the interventional device on a 2-D or 3-D CT image of the target object to produce a feedback image indicative of at least one of the identified positions of the interventional device in real time. The method can include displaying the feedback image for use to determine a position or to guide movement of the interventional device relative to the target object.

The full dose CT scan can use, or can be defined based on, a diagnostic dose level to achieve a predetermined signal to noise ratio (SNR) for the 2-D or 3-D CT image of the target object. The method can further include placing one or more fiducials within a region during the full dose CT scan and when acquiring the plurality of pairs of projections. The method can further include acquiring a 2-D or 3-D CT image of the target object using the full dose CT scan, prior to acquiring the plurality of pairs of projections of the interventional device. The target object can include at least one of a tumor, a duct, a lesion, a musculoskeletal structure, an organ, or a vessel. The 2-D or 3-D CT image of the target object can include a CT angiogram or an image of at least one of a tumor, vessel, duct, a lesion, an musculoskeletal structure, or an organ. The method can include generating the 2-D or 3-D CT image of the target object by incorporating at least one of a vascular image of a scanned region, a non-vascular image of the scanned region, a normal CT image of the scanned region. The method can include acquiring one or more 2-D or 3-D CT images of the target object over a full or partial respiratory cycle of a subject, at two extremes of a respiratory cycle of a subject, using the full dose CT scan over a time period of three to four seconds, or without respiratory suspension. The method can include determining positions of one or more fiducials during at least part of a respiratory cycle of a subject, using the one or more 2-D or 3-D CT images.

The method can include presenting the feedback image to a user in a format configured for at least one of stereoscopic viewing, cross-sectional viewing, fluoroscopic viewing, continuous mode viewing, or user-controlled image transition. The method can include presenting the feedback image to a user to include one or more of multiple views or CT slices of the feedback image, a view or a CT slice of the feedback image along a plane aligned with the interventional device, an indication of a distance relating the interventional device and the target device, an indication of previous positions of the interventional device, or navigational guidance or hint for moving the interventional device. The method can include acquiring each of the plurality of pairs of projections of the interventional device simultaneously using two x-ray source-detector pairs. The method can include configuring the acquisition of the plurality of pairs of projections of the interventional device as an acquisition of projections according to a CT scan dose reduction factor, compared to the full dose scan, comprising a value from a range of 2 to 492.

The interventional device can include a needle, probe, catheter, stent, balloon, forceps, internal anatomic structure, musculoskeletal structure, wire, internal orthopedic device, or shunt. Identifying the position of the interventional device using the back-projection can include locating an intersection of the back-projection. Forming the at least one 2-D or 3-D image of the interventional device can include using at least one of high pass filtering or thresholding. Forming the at least one 2-D or 3-D image of the interventional device can include using a set of time resolved images of the interventional device. Forming at least one 2-D or 3-D image of the interventional device can include using at least one of high pass filtering, image segmentation, thresholding, or subtraction of a projection associated with the full dose CT scan from a projection of the interventional device.

The method can include selecting, from a plurality of images of the target object, the 2-D or 3-D CT image of the target object on which to superimpose the at least one 2-D or 3-D image of the interventional device, according to one or more positions of one or more fiducials determined during at least part of a respiratory cycle of a subject. The method can include acquiring the plurality of pairs of projections while the gantry of the CT scanner is continuously rotated in a same direction. Superimposing the at least one 2-D or 3-D image on a 2-D or 3-D CT image of the target can include superimposing an endofluoroscopy image of the interventional/vascular device on an image of a vascular target object or a vascular road map. The image of the vascular target can be an image (e.g., pre-scanned or previously acquired image) obtained from higher doses of radiation than that for the image of the interventional/vascular device, or a composite image that can be constructed from repeated samples during the fluoroscopy procedure.

The method can include acquiring a further one or more 2-D or 3-D CT images of the target object without interrupting the acquisition of the plurality of pairs of projections of the interventional device. The method can further include acquiring a second plurality of pairs of projections of the interventional device using CT fluoroscopy, in response to the acquisition of the further one or more 2-D or 3-D CT images of the target object. The method can include increasing a signal to noise ratio (SNR) of the 2-D or 3-D CT image of the target object acquired prior to acquiring the plurality of pairs of projections of the interventional device, by registering the 2-D or 3-D CT image of the target object with one or more additional images of the target object. The method can include acquiring a further one or more 2-D or 3-D CT images of the target object while interrupting the CT fluoroscopy, responsive to detecting a movement of the target object that is non-respiratory or greater than a predefined movement threshold. The method can include acquiring a second plurality of pairs of projections of the interventional device using CT fluoroscopy, in response to the acquisition of the further one or more 2-D or 3-D CT images of the target. The method can include superimposing an updated 2-D or 3-D image formed of the interventional device, on a previously acquired 2-D or 3-D image of the target object, to produce an updated feedback image. The method can include rotating the feedback image for 2-D or 3-D visualization of at least one of the interventional device or the target object.

The method can include pulsing an X-ray source to perform the full dose CT scan and to acquire the plurality of pairs of projections of the interventional device using CT fluoroscopy. Acquiring the plurality of pairs of projections can include acquiring a plurality of subsets of two or more projections. The method can include acquiring the plurality of projections of the interventional device within a 50 degree angular rotation of the gantry of the CT scanner.

According to at least one aspect, a method for computed tomography (CT) fluoroscopy can include acquiring, by rotating an gantry of a CT scanner and using CT fluoroscopy, a plurality of projection images of an interventional device within a region of interest (ROI) at a first rate of angular projections per gantry rotation that is at least two times smaller than a second rate of angular projections per gantry rotation used for one or more full dose CT scans. The method can include identifying, for each of two or more projection images among the plurality of projection images, a corresponding image region indicative of the interventional device in each of the two or more projection images. The method can include determining, for the two or more projection images, a corresponding position of the interventional device in a three-dimensional (3-D) space associated with the ROI, using an intersection of representations of the corresponding image regions indicative of the interventional device when back projected into the 3-D space. The method can include superimposing, for the two or more projection images, a corresponding 2-D or 3-D image of the interventional device on a 2-D or 3-D CT image of the ROI according to the corresponding determined position of the interventional device to produce a 2-D or 3-D image illustrating a location of the interventional device relative to a target region within the ROI over time. The one or more 2-D or 3-D CT images of the ROI can be generated using projection data of the one or more full dose CT scans. The method can include displaying the produced 2-D or 3-D image for use to determine a position or to guide movement of the interventional device relative to the target region.

DETAILED DESCRIPTION

Figure 1:
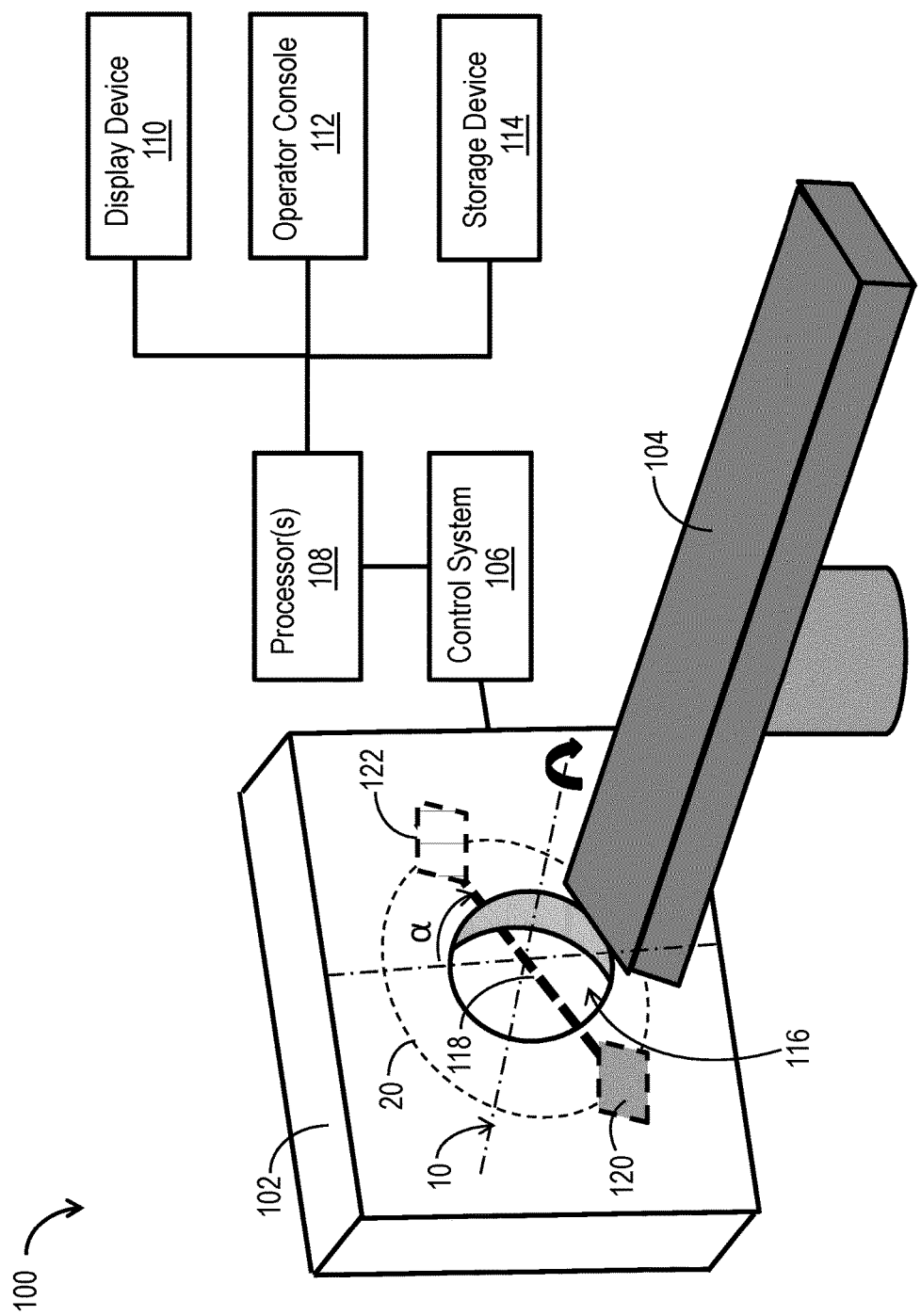
FIG. 1 is a diagram illustrating a rotational x-ray system, according to inventive concepts of this disclosure.

Computed tomography (CT) guided interventions are a mainstay of interventional radiology practices. Many important procedures are performed using CT guidance including biopsies, placement of drainage tubes and catheters, tumor ablation, musculoskeletal interventions, and many others. CT guided interventions allow for determination of appropriate puncture sites, direction of insertion of interventional device (e.g., needle), and placement of interventional device after each adjustment.

CT guided interventions can be performed using conventional CT (CCT) or CT fluoroscopy (CTF). When using CCT, a CT scanner usually performs full dose axial or helical scanning with the resulting scans having limited z-axis coverage. As used herein, a full dose scan refers to a CT scan using the conventional number of projection angles (typically 984) with sufficient dose to delineate a target of interest. The full dose scanning presents serious health risks for operators (e.g., physicians and/or health care practitioners) involved in the CCT procedures due to the potential cumulative radiation dosage acquired by these individuals over time. To mitigate such risks, during CCT procedures, operators make adjustments to the position of the interventional device and then step out of the room during scanning, repositioning based on the CT images, or rescanning. These steps of adjusting the interventional device, leaving the room, scanning the patient to evaluate the placement of the interventional device are repeated until the interventional device reaches a desired target. This approach makes the intervention procedure long, inconvenient and tedious for both the operator and the physician. For instance, the longer the intervention procedure is, the larger may be the sedation dose used and the more likely the patient will move adding more complexity and inaccuracy to the process of tracking the placement of the intervention device after successive adjustments. In addition, the longer the needle is inserted in the patient, the more likely certain complications are to arise such as infection, air leak, bile leak, and bleeding.

For CT fluoroscopy (CTF), CT scanners employ helical scanning and can acquire projections associated with several contiguous z-axis scan locations. Also, CTF is generally performed at the lowest possible milliamperage (mA) to visualize the target, critical anatomy, and the interventional device in an attempt to decrease radiation exposure to the patient and operator. This is usually approximately 20 mA in the chest in which most targets are high contrast as compared with the background because of surrounding air. Much higher doses are often used for the abdomen due to lower contrast differences between the target and background tissue. Typical mAs in the abdomen run from 40 to 200. In CTF, CT projections can be acquired either continuously or in a series of intermittent acquisitions between adjustments of the interventional device. For instance, the CT projections can be acquired responsive to activating a switch or a foot pedal. In general, operators remain in the room during CTF scanning and CTF images are displayed immediately after acquisition of CT projections. Regardless of the structure being imaged and targeted, typical CT fluoroscopic images are of very low quality, and the target and intervening critical structures can be difficult to visualize, thus decreasing confidence during interventional procedures. Even with the reduced milliamperage, e.g., compared to CCT, CTF-based interventional procedures still present a health risk for patients and operators who can accumulate a substantial radiation dose from several procedures over time.

There are several advantages of CTF over CCT. Because of the inefficiencies posed by operators walking in and out of the room after each position adjustment of the interventional device during CCT-based interventional procedures, fewer incremental adjustments are possible when using CCT. The relatively low number of possible incremental adjustment can lead operators to perform relatively large position adjustments or more extensive "blind" movements (e.g., without imaging guidance) of the interventional device. By way of contrast, CTF-based interventional procedures can be performed using near real-time CT-based guidance. Considering the relatively low milliamperage (e.g., compared to CCT) and the ease of use (e.g., operator, CTF seems to have the potential to substantially decrease procedure time, sedation requirements, costs, and the risk of potential complications. However, despite these advantages, the use of CTF has been largely abandoned in many CT imaging centers due to concerns over operators' (e.g., physicians, nurses, radiology technicians, or other healthcare practitioners involved in interventional procedures) safety due to radiation exposure—a particular problem in busy interventional practices.

In fact, in CCT-based and CTF-based interventional procedures, CT scanners usually use 984 separate projections to reconstruct composite CT images. This large number of projections per reconstructed image results in far more radiation (to patients and operators) than necessary to detect and localize high contrast interventional devices (e.g., needles, drainage tubes, catheters, probes, shunts, wire, stent, balloon, forceps, internal orthopedic device, or other interventional devices). Conventional CTF can take a series of conventional filtered back projection (FBP) images of the target and the interventional device, for example, at a rate equal to the gantry rotation speed. As such, the position of the interventional device is typically updated at 2 to 3 times per second. Due to the high attenuation of interventional devices like needles, the FBP reconstructions show significant reconstruction artifacts such as beam hardening. The accuracy of the position of the interventional device is also limited to the slice thickness of the reconstructed CT image.

In the current disclosure, ultra-low dose CT fluoroscopy technique that can reduce the radiation dose in CT fluoroscopy typically by a substantial factor (e.g., a factor between 2 and 500) compared to full dose CTF scanning. For example, the new fluoroscopy technique can enable performance of a whole radiology interventional procedure with less dose than that of a chest X-ray. The new fluoroscopy technique is sometimes referred as ultra-low dose CTF (ULD-CTF). The new fluoroscopy technique can be implemented, e.g., as a new mode of operation or process, on certain CT scanners.

The ULD-CTF technique is based on the realization that it is not necessary to use full doses to image high contrast objects like needles or other interventional devices. The ULD-CTF technique can make use of a fraction of the available projections during a single gantry rotation to detect the interventional device, therefore, resulting in radiation doses up to 500 times lower than radiation doses for conventional CTF scanning. For instance, when employing the ULD-CTF technique, a CT scanner can use a pair (or more generally, two or more) of CT projection images associated with different projection angles to reconstruct a position, an orientation, a shape, or a combination thereof of the interventional device. An angular difference of 90 degrees between the projection angles can allow for relatively high accuracy (e.g., compared to some other angular differences). However, angular difference (or angular separation) smaller than or larger than 90 degrees can also be used between each pair of (or consecutive pairs of the two or more) angular projections. In general, the angular separation can be greater than 0 degree and smaller than 180 degrees. A processor associated with the CT scanner can isolate (or identify) the interventional device in both CT projection images, and determine the position of the interventional device within 3-D volume space using the pair of CT projection images. The processor can overlay (or superimpose) a representation (or an image) of the interventional device on a previously acquired full dose CT 2-D or 3-D image of the target, according to the determined position of the interventional device in the 3-D volume space. The processor may apply motion correction schemes (or techniques) to the full dose CT 2-D or 3-D image(s) of the target to account for patient motion such as respiratory motion.

The processor can generate, in real time, a sequence of 2-D or 3-D images showing the placement of the interventional device relative to the target as the operator makes adjustments to the interventional device position. The ULD-CTF techniques described herein can allow for 4-D ULD-CTF with a time sequence of 3-D CT images showing both the target and the interventional device as output, or can allow for 3-D ULD-CTF with a time sequence of 2-D CT images of the target and the interventional device as output. As the x-ray source-detector pair of the x-ray scanner (or x-ray system) rotates, each pair of projections separated by some angle of, e.g., 5 to 175 degrees or 10 170 degrees, 30 to 150 degrees, can provide enough angular resolution to fully image the interventional device using backprojection of representations of the interventional device image in the two projections onto a previously acquired 2-D or 3-D image of the target. As the x-ray source-detector pair rotates, advancing pairs of projections or additional gantry rotation points are used to update (or track) the interventional device position in real time.

For example, in coronary or angiographic procedures, arterial injections can be performed using an interventional device using the methods and systems described herein. Catheterization is an example. Angiographic acquisition or scans of an interventional device can be outside of the heart where there is no cardiac motion for example, where there may be respiratory motion. The ULD-CTF technique can be used to generate a roadmap for the intervention procedure as well as allow for ongoing motion compensation. To obtain the roadmap, a breath-hold mode can for example be employed where sequential gantry revolutions are gated and interleaved to provide a full CT range of angles for reconstruction. The reconstruction can used filtered back projection (FBP) reconstruction at two phases of respiratory motion for instance, or a different method of reconstruction. This can be performed during an extended intra-arterial (IA) injection. The fluoroscopy technique can be used to perform reconstruction of the interventional device in real time, and to superimpose image(s) of the interventional device on a motion corrected coronary angiogram using a motion model. A motion model can be employed, for instance with scans of the target object at two extremes of respiratory motion, for motion correction. Mask (e.g., no contrast) acquisitions can be done at extremes of respiratory position so that registered mask subtraction can be done during the fill acquisition. For intravenous (IV) examinations, the fill acquisition can continue for around 20 seconds or some other suitable time periods. For intra-arterial examinations, the fill sequence can be on the order of 5 seconds or some other suitable time periods.

FBP refers to an analytic reconstruction algorithm that applies a convolution filter to remove blurring, and is used in cross-sectional image reconstruction. FBP utilizes simultaneous equations of ray sums taken at differing angles of a sine wave to compute the values of attenuation coefficients within a cross section. FBP is achieved via an algorithm of mathematical equations that can be solved by a high capacity computer. The attenuated profile or projection produced represented by a target anatomy is stored in the memory of the computer, solved and reconstructed. Each pixel (picture element) corresponds to the voxel (volume element) of the image. In some embodiments of the present methods and systems, FBP, adaptive statistical iterative reconstruction (ASIR), and/or model-based iterative reconstruction (MBIR) are not used.

FIG. 1 is a diagram illustrating one embodiment of a rotational X-ray system 100, according to inventive concepts of this disclosure. In brief overview, and by way of a non-limiting example, the rotational X-ray system 100 can include a CT scanner 102, a table 104 for accommodating a patient, a control system 106, one or more processors 108, a display device 110, an operator console 112, and/or a storage device 114.

The CT scanner 102 can for instance include a cavity 116, a gantry 118 mechanically coupled to an X-ray source assembly 120 on one of its ends and an X-ray detector array assembly 122 at its other end. The table 104 can slide toward and away from the CT scanner 102. In particular, the table 104 (supporting a subject or a patient) can slide into the cavity 116. The gantry 118 can rotate around a horizontal axis 10 of the cavity 116. As the gantry 118 rotates around the axis 10, the X-ray source assembly 120 and the X-ray detector array assembly 122 can move synchronously along a circular path 20 around the cavity 116. At any point in time, the x-ray source assembly 120 and the X-ray detector array assembly 122 can be aligned along a diameter of the circular path 20. As the gantry 118 rotates, the orientation (or angle α) between the diameter of the circular path 20 along which the X-ray source assembly 120 and the X-ray detector array assembly 122 are aligned and a reference orientation changes.

The rotations of the gantry 118 around the axis 10 can enable the x-ray source assembly 120 and the X-ray detector array assembly 122 to be oriented in different positions and angles (angle α) around the patient disposed on the table 104, while enabling a physician to perform procedures on to the patient. The x-ray source assembly 120 can emit a beam of x-rays which are directed at detector array assembly 122. Both assemblies 124 and 126 can be aligned and directed inward to the axis 10. The center ray of the emitted beam may pass through the center of the cavity 116. The emitted beam (or the center ray thereof) can be rotated about the center of the cavity 116 around the axis 10 during the acquisition of x-ray data from a subject (e.g., patient) placed on the table 104.

The beam of x-rays emitted by the x-ray source assembly 120 can impinge, e.g., after passing through the subject, on the detector array assembly 122. The detector array assembly 122 can include a two-dimensional array of detector elements. Each detector element produces an electrical signal that represents the intensity of an impinging X-ray and hence the attenuation of the X-ray as it passes through the subject. During a scan, control system 106 can cause the x-ray source assembly 120 and the detector array assembly 122 to rotate about the center of the cavity 116 to acquire X-ray attenuation projection data from different angles α. The detector array assembly 122 can be configured to acquire a number of projections, or views, per second which can be the limiting factor that determines how many views can be acquired for a prescribed scan path and speed.

The control system 106 can control the rotation of the assemblies 120 and 122 and the operation of the X-ray source associated with the X-ray source assembly 122. The control system 106 can include an X-ray controller (not shown in FIG. 1) that can provide power and timing signals to the X-ray source assembly 120. The x-ray controller can pulse on the x-ray source assembly 120 only at a selected subset of angles among the projections angles used in a full dose scanning. The control system 106 can include a data acquisition system (not shown in FIG. 1) that can sample data from the detector elements of the detector array assembly 122, and pass the data to the one or more processors 108. The control system 106 can also include a gantry motor controller (not shown in FIG. 1), e.g., for causing the gantry to rotate around the axis 10. The gantry motor controller can receive motion commands from the one or more processors 108 and provide power to the gantry 118 responsive to such commands.

The gantry 118, the X-ray source assembly 120, the detector array assembly 122, the table 104, and/or the control system 106 can be viewed as forming the CT or X-ray scanner device 102. The one or more processors 108, the display device 110, the operator console 112, and/or the storage device 114 can be integrated within the CT or X-ray scanner 102, integrated within a computing device communicatively coupled to the CT or X-ray scanner, or a combination thereof. The one or more processors 108 can execute computer code instructions to cause CT data acquisition, generate CT images based on CT acquisition data, cause display of generated CT images, store generated images or CT acquisition data in the storage device 114, or a combination thereof. The computer code instructions can include executable instructions associated with various CT data acquisition modes. The one or more processors 108 can receive an indication a CT data acquisition mode from the operator console 112, and execute the corresponding executable instructions.

The one or more processors 108 can receive digitized X-ray data from the control system 106 and perform image reconstruction according to the methods of the present disclosure. The one or more processors 108 can cause the reconstructed CT images to be displayed on the display device 110 or stored on the storage device 114. The one or more processors 108 can include a digital a central processing unit (CPU), a microprocessor, a digital signal processor (DSP), an image processor, an application-specific instruction set processor (ASIP), a graphics processing unit (GPU), a multi-core processor, or a combination thereof.

The one or more processors 108 can receive commands and/or scanning parameters from an operator via the operator console 112. The operator console 112 can include keyboard, a touch screen, a pedal, other manually operable controls, or a combination thereof. The display device 110 can include a display screen for displaying CT reconstructed images and/or other data to the operator of the CT or X-ray scanner. While FIG. 1 shows the CT or X-ray scanner 102 to include a single x-ray source assembly 120 and a single detector array assembly 122, the CT or X-ray scanner 102 can include two or more X-ray source-detector pairs arranged at offset angle(s) with respect to one another. In such a setup, two or more projections can be acquired simultaneously by the two or more x-ray source-detector pairs.

Figure 2:
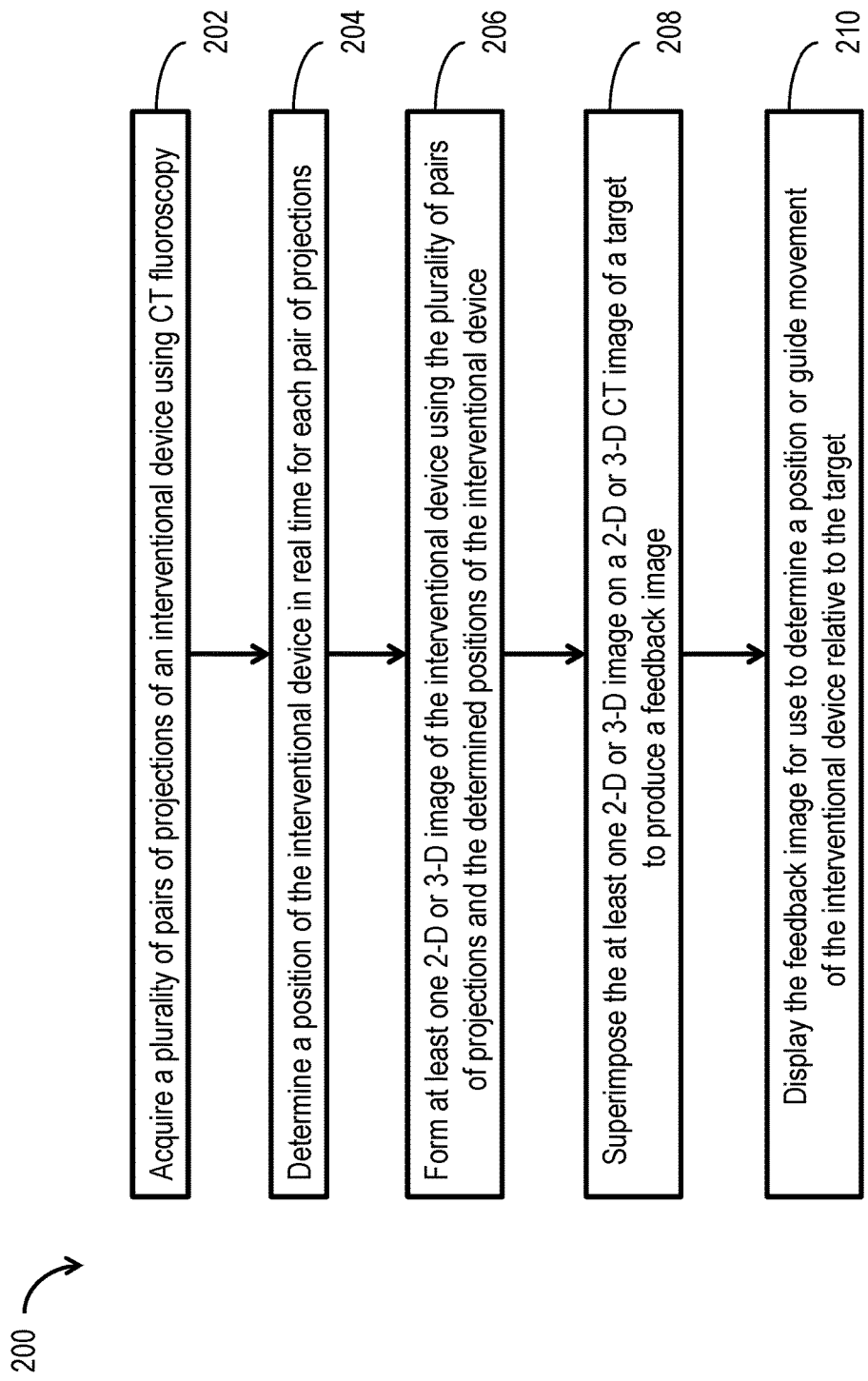
FIG. 2 is a flowchart illustrating a method for four-dimensional (4D) low dose computed tomography (CT) fluoroscopy, according to inventive concepts of this disclosure.

FIG. 2 is a flowchart illustrating a method 200 for ultra-low dose computed tomography fluoroscopy (ULD-CTF), according to inventive concepts of this disclosure. The ULD-CTF can be 4-D CTF that generates a sequence of 3-D CT images, or can be a 3-D CT fluoroscopy that generates a sequence of 2-D CT images. In brief overview, the method 200 can include acquiring a plurality of pairs of projections of an interventional device using CTF (step 202), identifying a position of the interventional device in real time for each pair of CT projections (step 204), and forming at least one representation of the interventional device using the plurality of pairs of projections and the identified positions of the interventional device (step 206). The method 200 can also include superimposing (or overlaying) the at least one CT image of the interventional device on a CT image of a target to produce a feedback image (step 208) and displaying the feedback image for use to determine a position or guide movement of the interventional device relative to the target (step 210).

Referring to FIGS. 1 and 2, the one or more processors 108 can cause the CT or x-ray scanner to acquire, prior to acquiring the plurality of pairs of projections, a first set of CT projections (or projection images) using one or more full dose CT scans of the subject (or an anatomical region thereof). The first set of CT projections can be used to generate one or more 3-D CT images or one or more 2-D CT images of the an anatomical region of the subject including a target anatomical structure (referred to herein as target). The target object can include a tumor, a lesion, an anomaly, a musculoskeletal structure, an organ, a duct, a blood vessel, or a combination thereof. The one or more processors 108 can reconstruct a sequence of 2-D images, for example, by applying FBP to the first set of acquired CT projection images. The one or more processors 108 can generate one or more 3-D images of the anatomical regions including the target using the reconstructed sequence of 2-D images.

In some implementations, the first set of CT projections (prior to use, introduction, insertion, monitoring or penetration of the interventional device) can be associated with at least two respiratory states of the subject. For example, the CT scanner 102 can acquire a first subset (of the first set) of CT projections at a first respiratory state (e.g., deep inhale) of the subject and a second subset (of the first set) of CT projections at a second respiratory state (e.g., deep exhale) of the subject. The one or more processors 108 can construct a first 3-D image (depicting a 3-D volume of the anatomical region and the target at the first respiratory state) using the first subset of CT projections, and a second 3-D image (depicting a 3-D volume of the anatomical region and the target at the second respiratory state) using the second subset of CT projections. The one or more processors 108 can further generate additional 3-D images corresponding to additional respiratory states intermediate to the first and second respiratory states. The one or more processors 108 can perform 3-D to 3-D registration between first and second 3-D images to estimate a vector field describing the elastic deformation of the anatomical region and the target. By scaling the vector field, intermediary respiratory states in between full inspiration and expiration can be simulated.

The full dose CT scan(s) can be defined by a diagnostic dose level and the number of angular projections. For instance, in a full dose CT scan, the CT or X-ray scanner 102 can perform 984 projections (e.g., corresponding to 984 angles for the x-ray source-detector pair). In general, the number of projections in a full dose CT scan can be defined based on a minimum number of projections required to achieve adequate image quality of the reconstructed 2-D or 3-D CT images and/or allow for reliable diagnosis by a healthcare provider. In some implementations, the full dose CT scan can use, or can be defined based on, a diagnostic dose level to achieve a predetermined signal to noise ratio (SNR) for the 2-D or 3-D CT image of the target object. The CT or X-ray scanner 102 can acquire the first set of projections associated with the full dose CT scan over a time period of three to four seconds for instance (or any other specified time period).

The CT or X-ray scanner 102 can acquire the first set of CT projections for generating one or more CT 2-D or 3-D CT images of the target object without respiratory suspension. The CT or X-ray scanner 102 can acquire the first set of CT projections for generating the one or more 2-D or 3-D CT images of the target over a full or partial respiratory cycle of the subject. For instance, performing the full dose CT scan(s) can include placing one or more fiducials within a region (e.g., on the skin of the subject) scanned by the CT or X-ray scanner 102. The one or more fiducials can act as references for detecting subject movement (e.g., respiratory movement). In particular, movement of a fiducial from one CT image to another can be indicative of a movement of the subject or the target.

The one or more processors 108 can store a library of 3-D and/or 2-D images associated with distinct respiratory states in a memory or in the storage device 114. The library of 3-D and/or 2-D images can include images associated with deep inhale, deep exhale, and intermediate interpolations, or can include various images associated with distinct respiratory states based on fiducials' positions.

The method 200 can include the CT or X-ray scanner 102 acquiring a plurality of pairs of projections of an interventional device using CTF and by rotating the gantry 118 of the CT or X-ray scanner 102 (step 202). The interventional device can include a needle, probe, catheter, shunt, drainage tube, wire, stent, balloon, forceps, internal orthopedic device, or the like. Each pair of the projections can be obtained at a predetermined (or predefined) angular separation, for example, within a range of 10 to 170 degrees. In some implementations, the predetermined (or predefined) angular separation can be about 90 degrees (e.g., between 80 and 100 degrees). In the full CT scan(s) the angular separation between consecutive projection angles can be substantially smaller than the predetermined angular separation associated with each of the plurality of pairs of projections. For instance, the full dose CT scan can include acquiring 984 projections per revolution at equal angle increments (or adjacent angle separation) of 360/984 degree. The predetermined angular separation can be greater than (e.g., a multiple of) the angular separation between consecutive projection angles used for the full dose CT scan. As such, the total number of projections acquired using ULD-CTF (or at step 202) can be substantially smaller (e.g., at least by a factor of 10) than the number of CT projections acquired during the full dose CT scan. For instance, using a 30 degree separation can lead to a possible maximum number of projection angles per gantry rotation equal to 360/30=12 (e.g., 6 projection frames per revolution with each projection frame formed using a corresponding pair of projections) with a single plane CT scanner, in which case an overall dose reduction factor equal to 984/12=82 can be achieved. Such a reduction can substantially decrease the radiation dose or exposure to the subject and the operator performing the interventional procedure. Using a separation angle equal to 30 degrees and a revolution rate of 2/sec can lead to maximum frame rate of 6 frames per revolution or 12 frames per second (each frame generated using a corresponding pair of projections). In the acquisition of the plurality of pairs of projections of the interventional device, the total number of acquired projections can be selected or predetermined to achieve a CT scan dose reduction factor with a value ranging, for example, from 2 to 492. For instance, the CT scanner 102 can acquire a single pair of projections (e.g., with 90 degrees angular separation) per gantry revolution, therefore, achieving a 492 dose reduction factor. In the case where the CT or X-ray scanner 102 is a bi-plane scanner having two X-ray source-detector pairs (e.g., two X-ray source assemblies 124 and two detector array assemblies), the CT or X-ray scanner 102 can acquire each pair of projections of the interventional device simultaneously using the two X-ray source-detector pairs.

Figure 3:
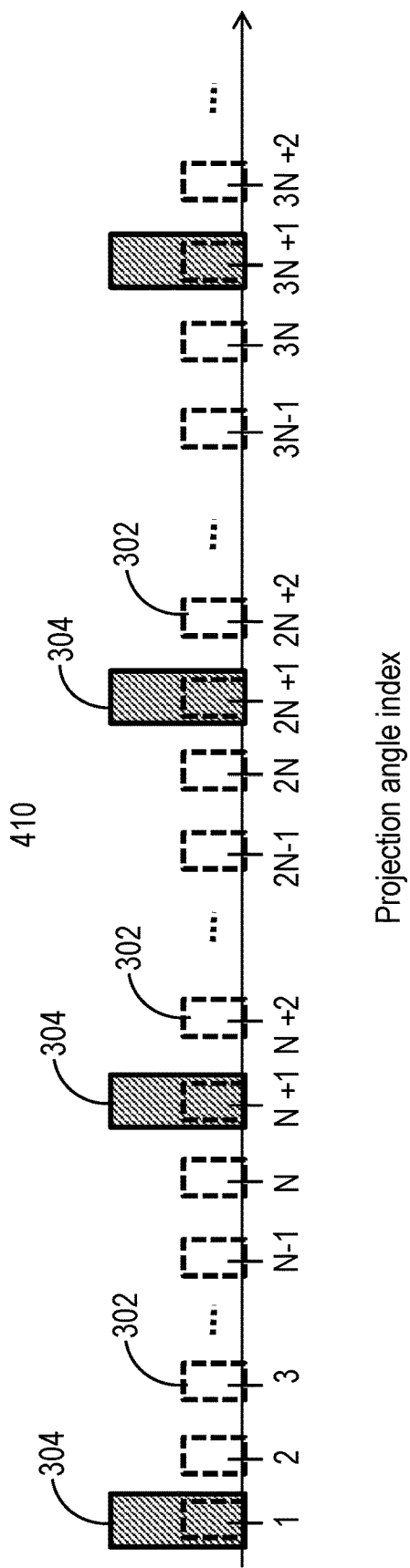
FIG. 3 shows a diagram illustrating an example configuration of pulsing for a full dose scan and an ultra-low dose CT fluoroscopy (ULD-CTF) scan, according to inventive concepts of this disclosure.

FIG. 3 depicts a representation of an example configuration of pulsing for a full dose scan and a ULD-CTF scan, according to inventive concepts of this disclosure. The x-axis represents the index of projections angles. The dashed pulses 302 can represent pulses that the X-ray controller can apply to the X-ray source assembly 120 during the full dose scan. As shown in FIG. 3, the X-ray or CT scanner 102 can acquire a projection at each available projection angle. The hashed pulses 304 can represent pulses that the X-ray controller can apply to the X-ray source assembly 120 during the ULD-CTF scan. The X-ray controller or the X-ray source assembly 120 can skip N projections angles between each pair of CTF projections, leading to a CT scan dose reduction factor equal to N. The number N can be an integer between 2 and K/2 where K is the total number of projections acquired in the full dose CT scan. The X-ray controller can select a subset of the projection angles associated with the full dose scan for use to perform projections during the ULD-CTF procedure. The selected subset of the projection angles can be associated with a CT scan dose reduction factor equal to N, and can include pairs of projection angles with each pair separated by the predetermined (or predefined) angular separation.

The method 200 can include identifying a position of the interventional device in real time for each pair of projections (step 204). Each pair of projections can be separated by the predefined (or predetermined) angular separation, e.g., 10-170 degrees, and can provide sufficient angular resolution to fully image the interventional device (e.g., needle or other high contrast device) using back projection of a representation of the interventional device image in the two projections onto a 2-D or a 3-D image of the anatomical region including the target. For instance, the data acquisition system can arrange the selected subset of projection angles used in CT fluoroscopy into pairs where each pair of projection angles are separated by the predefined (or predetermined) angular separation (e.g., about 90 degrees).

The one or more processors 108 can register each (or at least one) of the pairs of projection images to a 2-D or 3-D image associated with the full dose scan. For instance, the one or more processors 108 can register a pair of projection images to a 3-D image associated with a respiratory state among a library of 3-D images associated with various respiratory states. The one or more processors 108 can use a registration scheme to estimate a deformation scaling factor which maximizes the similarity between the acquired pair of projection images and the 3-D image associated with a corresponding respiratory state. The one or more processors 108 may determine the deformation scaling factor minimizing a mean squared error (MSE) using, for example, a gradient descent approach. In some implementations, the one or more processors 108 can register the pair of projection images to a 3-D image associated with a respective respiratory state based on the fiducials' locations in the 3-D image and in the pair of projection images (e.g., the fiducials are also used when acquiring the pairs of projection images). The registration of the pair of projection images to a 3-D image associated with a corresponding respiratory allows for motion correction when constructing a 2-D or 3D image comprising both the target and the interventional device.

The one or more processors 108 can identify (or isolate) the interventional device within each of the pairs of projection images. The one or more processors 108 can identify (or isolate), within each pair of projection images, a corresponding image region representing the interventional device. For example, the one or more processors 108 can identify, for each of the pairs of projection images, a corresponding mask (e.g., representing the anatomical region and target, but not the interventional device) to be subtracted from that projection image. For each projection image of a pair of projection images, the corresponding mask can be a 2-D projection image with a similar projection angle from the first set of projection images acquired during the full dose scan(s). Due to variations in the starting angle of each gantry revolution, the one or more processors 108 may generate a mask by interpolating two projection images acquired during the full dose scan(s) and associated with adjacent projection angles. The one or more processors 108 may use the registration of the pair of projection images to the 3-D image to identify the proper mask(s). The one or more processors 108 may also perform a sub-pixel deformable local registration to fully remove (or mitigate) relatively small registration error caused by fiducials or anatomical structures. The one or more processors 108 can subtract from each projection image of the pair of projection images the corresponding mask to isolate the image portion (in that projection image) representing the interventional device.

In some implementations, the one or more processors 108 can perform segmentation within the pair of projection images to isolate the image regions representative of the interventional device. The one or more processors 108 can employ high pass filtering and thresholding in performing the segmentation and isolating the image regions representing the interventional device. Isolating the interventional device (or the corresponding image regions) within the pair of projection images can eliminate background information to emphasize or retain image information indicative of the interventional device in both projection images.

The one or more processors 108 can apply global thresholding to the pair of projection images after isolating the image regions representing the interventional device. The one or more processors 108 can apply a topology preserving thinning to the isolated image regions (or other automatic centerline computation techniques known in the art) to extract (or determine) the centerline segments of the interventional device in the pair of projection images. In each projection image of a pair of projection images, a centerline segment that is equidistant from the surface of the interventional device (or from the sides of the corresponding image region) within that projection image is determined by the one or more processors 108.

Figure 4:
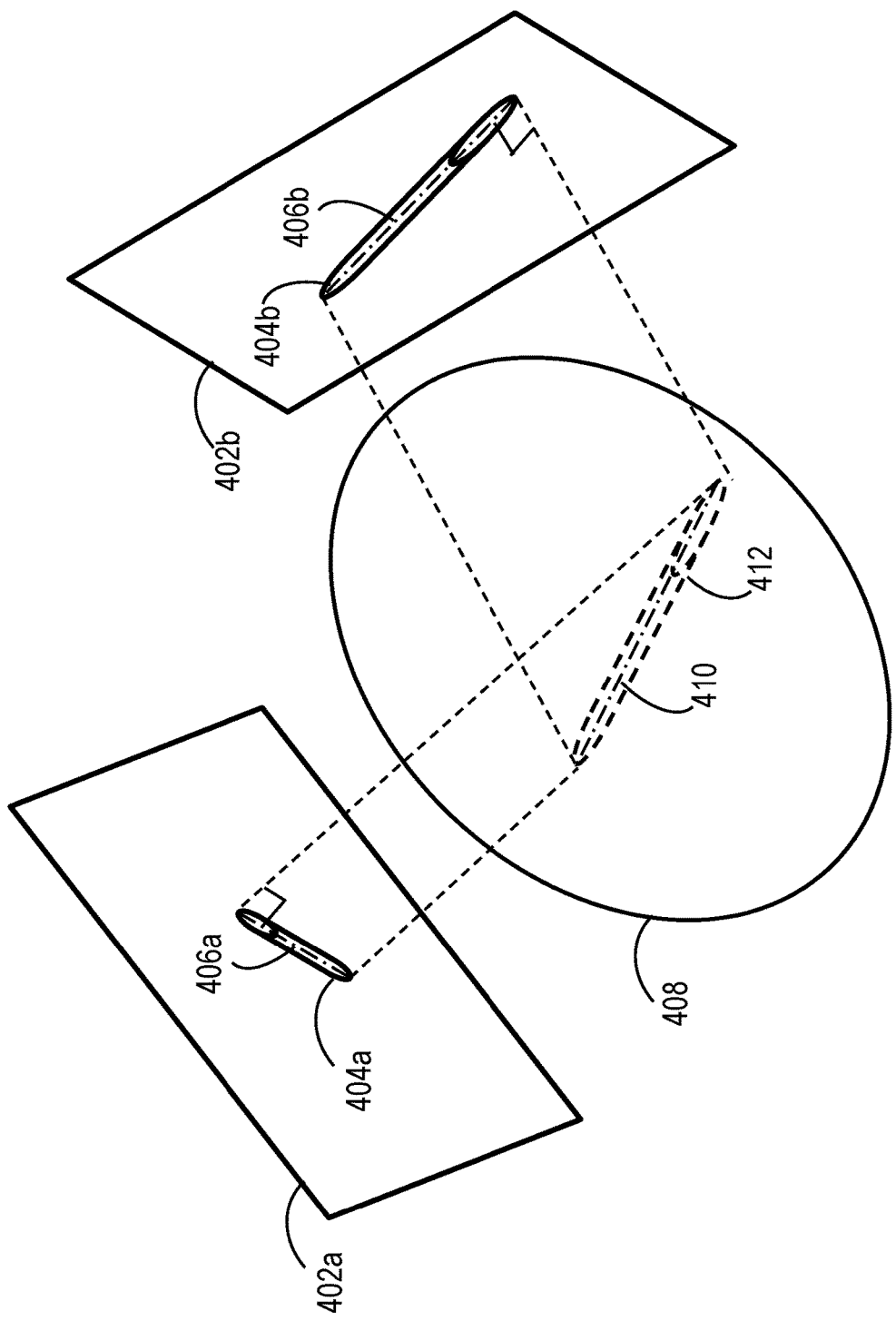
FIG. 4 is a diagram illustrating identification of the position of an interventional device using a pair of acquired projections, according to inventive concepts of this disclosure.

FIG. 4 is a diagram illustrating the identification of a position of the interventional device using a pair of acquired projections, according to inventive concepts of this disclosure. A first projection image 402*a* and a second projection image can each include a corresponding image region 404*a* and 404*b*, respectively, representing the interventional device. A centerline segment 406*a* of the interventional device in the first projection image 402*a* can be determined (by the one or more processors 108) based on the image region 404*a*, as described above. Also, a centerline segment 406*b* of the interventional device in the second projection image 402*b* can be determined (by the one or more processors) based on the image region 404*b*. The 3-D volume space 408 can represent a volume space associated with a 3-D image of the anatomical region and the target generated based on full dose scan data. The 3-D volume space 408 can represent a 3-D image of the anatomical region and the target associated with a respiratory state of the subject.

The one or more processors 108 can back project the image regions 404*a* and 404*b* into the 3-D volume space 408. Back projecting the image region 404*a* can include the one or more processors 108 back projecting the centerline segment 406*a* along a plane orthogonal to the projection image 402*a*. Back projecting the image region 404*b* can include the one or more processors 108 back projecting the centerline segment 306*b* along a plane orthogonal to the projection image 402*b*. For instance, the one or more processors 108 can register each end of the centerline segment 406*a* to a corresponding end of the centerline segment 406*b*. The one or more processors 108 can determine the intersection between the back projections of both centerlines 406*a* and 406*b*. Determining the intersection between the back projections of centerlines 406*a* and 406*b* can include registering each end of the centerline segment 406*a* to a corresponding end of the centerline segment 406*b*, and determining the intersections between back projections of corresponding ends of the centerline segment 406*a* and the centerline segment 406*b*.

The intersection between the back projection of the centerline segment 406*a* and the back projection of the centerline segment 406*b* defines the centerline segment 410 of the interventional device within the 3-D volume space 408. As such, the one or more processors 108 can identify the centerline segment 410 by determining the intersection between the back projection of the centerline segment 406*a* and the back projection of the centerline segment 406*b*. By identifying the centerline segment 410, the one or more processors 108 in fact identify a position and an orientation of the interventional device in the 3-D volume space 408. For instance, the centerline segment 410 can define the image region 412 representing the interventional device within the 3-D volume space 408.

In some implementations, the one or more processors 108 can register one or more pixels (or blocks of pixels) of the image region 404*a* to one or more pixels (or blocks/groups of pixels) of the image region 404*b*. The one or more processors 108 can back project the pixels (or blocks/groups of pixels) of the image regions 404*a* and 404*b* that are registered to one another into the 3-D volume space 308. The one or more processors 108 can determine the intersections between the back projections of pixels (or blocks of pixels) that are registered to each other within the 3-D volume space 308. The determined intersections represent pixels (or blocks/groups of pixels) of the interventional device within the 3-D volume space 308. Accordingly, the one or more processors 108 can determine the position of the interventional device within the 3-D volume space 308 by determining such intersections.

The method 200 can further include the one or more processors 108 registering the pair of projections images 402*a* and 402B to a 3-D image associated with a respiratory of the subject prior to determining the position of the interventional device. The one or more processors 108 can determine positions of one or more fiducials. The one or more processors 108 can back project image regions representative of a fiducial within each of the pair of projection images onto various 3-D images associated with various corresponding respiratory states of the subject. The one or more processors 108 can register the pair of projection images 402*a* and 402*b* to the 3-D image for which the intersection of the back projections of the fiducial (from the pair of projection images 402*a* and 402*b*) matches or overlaps with the same fiducial in that 3-D image.

Referring back to FIGS. 1 and 2, the method 200 can include the one or more processors 108 forming at least one 2-D or 3-D image of the interventional device using the plurality of pairs of projections and/or the identified positions of the interventional device (step 206). The one or more processors 108 can use one or more of the isolated image regions (e.g., image regions 404*a* and 404*b*) representative of the interventional device within the acquired pairs of projection images to reconstruct at least one 2-D or 3-D image of the interventional device. The one or more processors 108 can extract one or more of the image regions representative of the interventional device (e.g., image region(s) 404*a* and/or 404*b*) and use such image region(s) as 2-D image(s) of the interventional device. The one or more processors 108 can reconstruct one or more 2-D or 3-D images of the interventional device using the extracted image region(s), such as image region(s) 404*a* and/or 404*b*. In some implementations, the one or more processors 108 may store one or more 2-D or 3-D images of the interventional device in a database or in the storage device 114 for retrieval to overlay (or superimpose) on 3-D images of the anatomical region and the target. In some implementations, forming a 2-D or 3-D image of the interventional device can include selecting and/or retrieving an image of the interventional device from the database or the storage device 114, and rotating (or more generally applying a transformation to) the retrieved image to conform with a determined orientation of the interventional device in the 3-D volume space 408.

The one or more processors 108 can form at least one 2-D or 3-D image of one or more fiducials. The one or more processors 108 can either form 2-D or 3-D images including both the fiducials and the interventional device, or can form separate 2-D or 3-D images for the fiducials and the interventional device. For instance, the one or more processors 108 can form the 2-D or 3-D images of the fiducials in a similar way as discussed above with regard to forming an image of the interventional device The method 200 can include superimposing (or overlaying) the at least one 2-D or 3D image of the interventional device on a 2-D or 3-D CT image of a target object, to produce a feedback image (step 208). The feedback image can include the anatomical region, the target, and the interventional device. The one or more processors 108 can overlay (or superimpose), for each pair of projection images (such as projection images 402 and 402*b*), a 3-D image of the interventional device on a 3-D image of the anatomical region and the target registered to that pair of projection images, according to the determined position of the interventional device within the 3-D image (or within the 3-D volume space 408). The one or more processors 108 can overlay (or superimpose), for each pair of projection images (such as projection images 402 and 402*b*), a 2-D image of the interventional device on a 2-D image of the anatomical region and the target registered to that pair of projection images, according to the determined position of the interventional device at step 204.

A plurality of 2-D or 3-D images of the target object (and corresponding fiducials) may be established or obtained across different phases of a respiratory and/or cardiac cycle, and can be stored in a library of images. As discussed above, the one or more processors 108 can match fiducial positions in the pair of projection images (images of the interventional device) with fiducial positions in one of the plurality of images of the target object or determine a deformation scaling factor for minimizing a mean squared error (MSE) to select a 2-D or 3-D image of the target object to which the pair of projection images 402*a* and 402*b* are registered. During the set-up scan, the CT or x-ray scanner 102 can acquire three or four seconds of full dose exposure before the interventional device (e.g., needle) placement begins. Fiducials can be placed on the surface of the patient. These fiducials can optionally be made from crossed needles or similar contrast objects (including anatomic internal structures such as surgical clips, calcified vessels or organs) so that they can be segmented in the same way that the interventional device is segmented. The CT or X-ray scanner 102 can perform scans with free breathing so that the entire respiratory cycle is sampled. For each revolution, for instance, the one or more processors 108 can reconstruct the fiducial position in 3-D. For each revolution, the one or more processors 108 can acquire and store a corresponding full dose 2-D or 3-D target image for each fiducial position. For each position of the fiducials, the one or more processors 108 can select the corresponding target object (or subject) image(s) on which to superimpose the 2-D or 3-D image of the interventional device depicting the real-time position of the interventional device determined at step 204. In other words, by comparing a fiducial's position within a current 2-D or 3-D image of the interventional device and the fiducial's positions within the 2-D or 3D CT images of the target object, the one or more processors can select the appropriate 2-D or 3-D CT image of the target object on which to superimpose (or combine with) a current 2-D or 3-D image of the interventional device. The one or more processors 108 can compare fiducials' locations within consecutive 2-D or 3-D images of the interventional device (or back project fiducials within a 2-D or 3-D image of the interventional device onto a corresponding 2-D or 3-D CT image of the target) to detect substantial (e.g., greater than a threshold value) non-respiratory subject movement. Upon such detection, the one or more processors 108 may warn the healthcare practitioner performing the intervention procedure that that the patient/target has moved in between scans for instance, to prompt him to take another setup (or full dose) scan.

The one or more processors 108 can overlay the image of the interventional device formed at step 206 on the image of the target object registered to the pair of projection images 402*a* and 402*b*. Superimposing or combining the image of the interventional device can include the one or more processors 108 identifying an image region (e.g., image region 412 in FIG. 4) within the image of the target object based on the determined position (or determined centerline segment 410) of the interventional device within that image, and modifying (or setting) pixel values within the identified image region 412 using the image of the interventional device. For instance, pixel values within the identified image region 412 can be modified or set to be equal to values of corresponding pixels in the image of the interventional device formed at step 406. Superimposing the 2-D or 3-D image of the interventional device can include overlaying a 2-D or 3D image of the interventional device on the image of the target object along the centerline segment 410. Superimposing the 2-D or 3-D image of the interventional device on the selected 2-D or 3-D CT image of the target object can include overlaying or inserting (e.g., by changing pixel values) an endofluoroscopy image of the interventional device on the image of anatomical region and the target, for example. The interventional device can include a vascular device, and the target object can include a vascular target object or a vascular road map. The image of the vascular target object can be an image (e.g., pre-scanned or previously acquired or reconstructed image) obtained using full dose scanning projections, or an image that is constructed from repeated samples (or projections) acquired during the fluoroscopy (or ULD-CTF) procedure.

By back projecting the interventional device from a pair of projection images onto a 3-D image of the target and superimposing a 2-D or 3-D image of the interventional device on the 3-D image of the target, the one or more processors 108 can generate a feedback image that accurately shows the instant or real time position of the placement of the interventional device relative to the target based on as little as a pair of projections. The generation of the feedback image does not necessarily involve performing FBP or other conventional CT image reconstruction methods that typically require a relatively large number of CT projections and which suffer from some image reconstruction artifacts. Also, the ULD-CTF imaging approach (e.g., by determining the position of the interventional device and incorporating an image of the interventional device at the determined position) described above allows for using the entire z-axis available on the CT scanner 102 without additional CT projections or additional complexity. Using the entire z-axis allows for keeping the interventional device in view during the interventional procedure, reconstructing images along the longitudinal axis of the interventional device, and accurately estimating (or determining) the distance between a tip of the interventional device and the target. The ULD-CTF imaging approach also eliminates beam hardening artifacts associated with conventional reconstruction techniques, such as FBP. With CCT, using the whole z-axis would entail performing a conventional CT scan through the same volume and performing CT image reconstruction (e.g., using FBP). Such conventional approach would call for a comparatively larger dose of radiation.

The method 200 can include displaying the feedback image on a display device for use to determine a position of, or to guide movement of the interventional device relative to the target (step 210). The one or more processors 108 can cause the feedback image to be displayed, for example, on the display device 110. The one or more processors 108 can display (or render) 2-D slices of a 3-D feedback image, or can display the feedback image as a 3-D image. The one or more processors 108 can cause the display device 110 to display the feedback images in at least one of various ways. For example, the display device 110 can render a single CT slice, or a series of CT slices, oriented in axial, coronal, or sagittal position. Considering that the entire z-axis of the CT scanner 102 can be used, the one or more processors 108 (e.g., automatically or responsive to a selection by the operator) may cause the display device 110 to provide a view along a longitudinal axis of the interventional device or a short axis of the interventional device (periscope view). If the displayed image is oriented along the longitudinal axis of the interventional device, the operator would be viewing the anatomy along the projected interventional device path. As such, the interventional device would be within the imaging plane (a particular problem with CT fluoroscopy as it exists today) during the interventional procedure. The one or more processors 108 can display the feedback image in a format configured for at least one of continuous mode viewing, fluoroscopic viewing, user-controlled image transition, cross-sectional viewing, stereoscopic viewing, or a combination thereof.

For instance, in a continuous mode viewing, the CT scanner 102 can continuously acquire pairs of projections at a predefined angular separation, and the one or more processors 108 can continuously generate a feedback image for each acquired pair of projections for instance. The one or more processors 108 can display the sequence of generated feedback images or 2-D slices thereof in real time (immediately after acquisition of each pair of CT projections) as the operator adjusts the placement of orientation of the interventional device. In a fluoroscopic viewing mode, the operator can step on a pedal or press a button for example, to trigger acquisition of each pair of projections and/or display of corresponding generated feedback images (or 2-D slices thereof). The one or more processors 108 and/or the display device 110 may allow for user-controlled image transition. The operator may step on a pedal, press a button, tap or slide on a touch screen, or activate another type of trigger to cause the display device 110 to transition from one displayed image to another. In a cross-sectional viewing mode, the display device 110 can render cross-sectional slices of the anatomical region or the target object. In stereoscopic viewing (or rendering), the display device 110 can render the interventional device and the anatomical region (including the target) stereoscopically. For example, the one or more processors 108 can generate anaglyph stereo feedback images that can be viewed with red and blue glasses. The operator can use a set of bifocals with the top half being clear and the bifocal lenses are red and blue, for instance. The display device 110 may display the feedback images according to a side by side stereoscopic view at slightly different angles.

Figure 5:
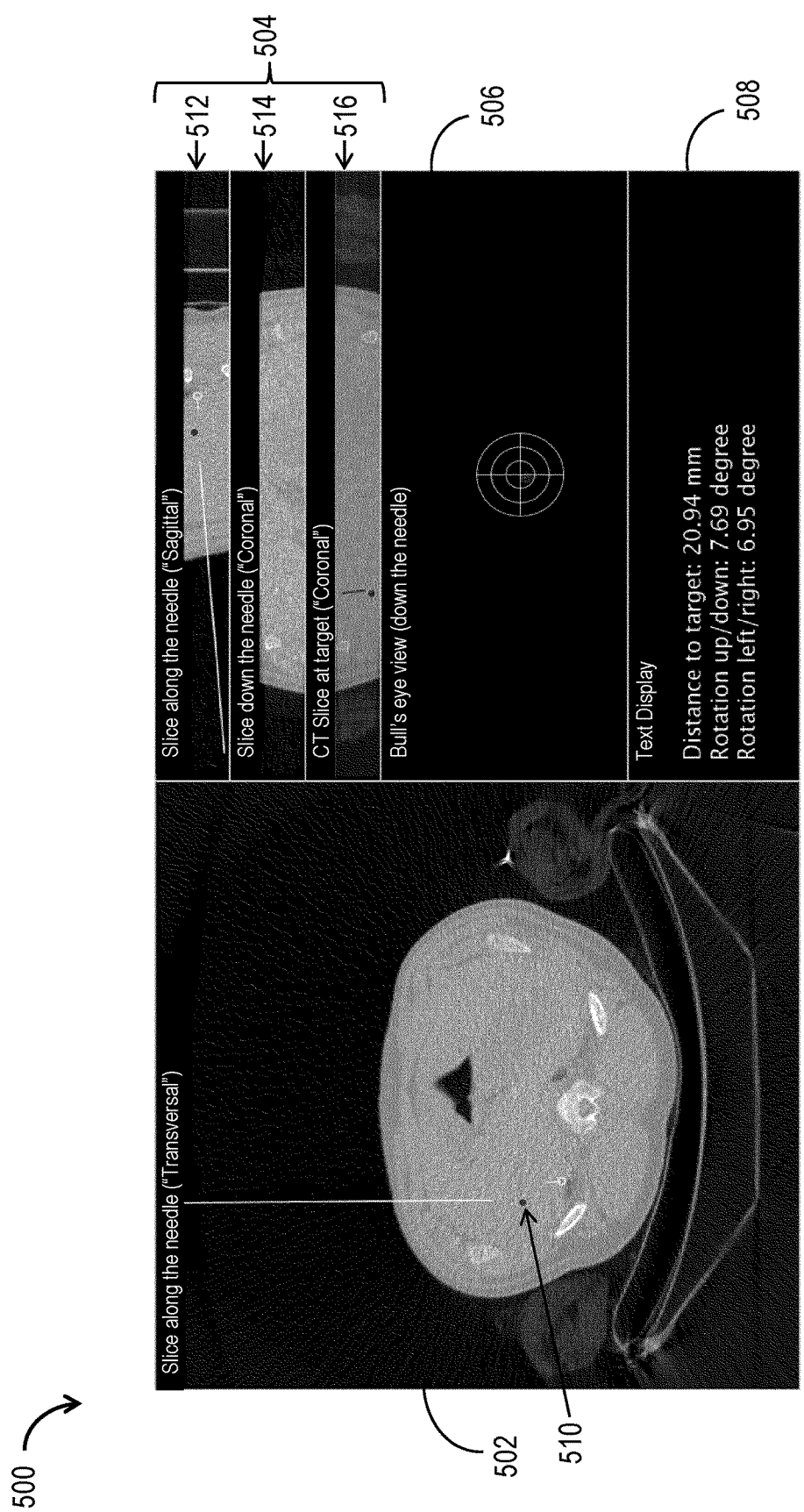
FIG. 5 shows example display options for displaying feedback images, according to example embodiments of the current disclosure.

FIG. 5 shows example display options for displaying feedback images, according to example embodiments of the current disclosure. The display options can include a first display option 502 for rendering a view (or a CT slice) along a plane aligned with the interventional device (needle), a second display option 504 for rendering multiple views or CT slices, a third display option for rendering 506 a bull's eye, and fourth display option 508 for rendering text output. The display device 110 can render a feedback image according to any combination of the display options 502-508.

According to the display option 502, a processor 108 can select a slice or a sectional view of the feedback image along a plane aligned with (or associated with) the interventional device (e.g., needle) and the display device 110 can render the selected slice or sectional view. The display device 110 may render a tip of the interventional device or the target object 510 with a distinct color (e.g., red, yellow, blue, or other colors) than the anatomical region shown in the selected view or slice. The display device 110 may assign different colors to the tip of interventional device (or a projection thereof) and the target object 510. According to the display option 504, the display device 110 can simultaneously render (or provide for rendering upon selection) various views, such as a 3-D view, one or more sectional views (or slices), or a combination thereof. For instance, the sectional views or slices can include a slice or sectional view 512 along a plane aligned with (or associated with) the interventional device, a slice or sectional view 514 down the interventional device, a slice or sectional view 516 at the target object 510, and/or other sectional views or slices. The target object 510 (e.g., a tumor, a duct, a lesion, a blood vessel, or other anatomical structure) may be pre-selected by the operator (e.g., a physician) and located in space for all subsequent images.

The display device 110 may display an entire slab (3D space or volume), as part of the display 502 or display option 504, with the target object marked by the operator on images acquired during setup (full dose) scans. In some implementations, the entire interventional procedure could be performed using "slab view" with no actual slice data displayed. Such a display approach may work well in organs with less critical anatomy intervening between the interventional device and the target object. The display device 110 may continually update a CT slice or sectional view (e.g., a slice along the longitudinal axis of the interventional device), for example, based on new acquired ULD-CTF projections. Such rendering approach would give the operator a CT "road map" of the anatomy, for example, along a plane aligned with the interventional device. The display device 110 may allow the operator to select a view or slice, from multiple available views, for rendering with higher resolution or with interactive options (e.g., rotating, zooming in, zooming out, or a combination thereof). When displaying a 3-D feedback image, the display device 110 can allow the operator to rotate the displayed image around one or more axes, zoom in, zoom out, slide the image, or a combination thereof.

According to display option 506, the display device 110 can render a dot or mark representing the target object location and concentric circles target with a corresponding center representing the location of the tip of the interventional device (or a projection thereof). The concentric circles target can illustrate visually the direction of the interventional device relative to the location of the target object. According to the display option 508, the display device 110 can display, e.g., in real-time, updates of the distance and direction from an end of the interventional device (e.g., needle tip) to the target object. The display device 110 can display text indicative of the distance between the tip of the interventional device and the target object, and orientation adjustments (e.g., rotation angles) to adjust the direction of the interventional device toward the target. The one or more processors 108 can cause the display device 110 to update content rendered according to any of the rendering options 502-508 in real time (e.g., immediately after a new pair of projections is acquired). The display device 110 can allow for display of one or more indications of previous positions of the interventional device (e.g., an image of a path traveled by the interventional device within the anatomical region).

The operator, such as healthcare professional performing the intervention procedure on the subject, can use the displayed feedback image and/or other displayed data to determine a current position of the interventional device (e.g., with respect to the target object), or to assess or modify the path of the interventional device through the subject. For example, the operator can use the data (e.g., slices or views associated with the feedback image, bull's eye view, textual information, or a combination thereof) displayed in real time to track and/or guide movement of the interventional device. The operator can, for example, adjust the orientation of the interventional device based on displayed textual orientation adjustments, bull's eye view, or a rendered slice image.

Figure 6C:
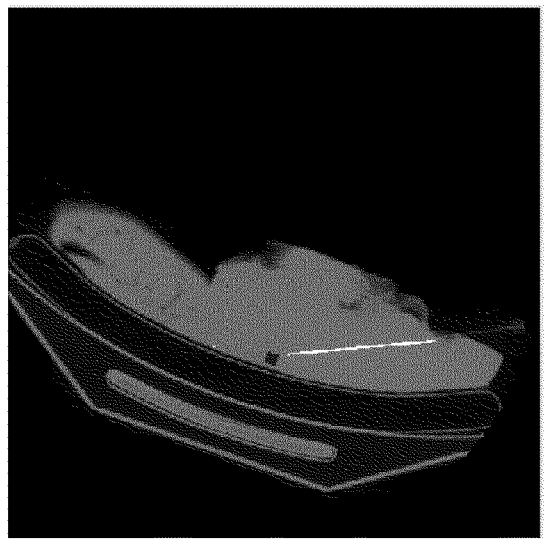
FIGS. 6A-6C show examples of CT images generated as part of an experimental CT fluoroscopy procedure performed on a live pig and illustrating progressive advancement of a needle toward a target, according to inventive concepts of the current disclosure.
Figure 6B:
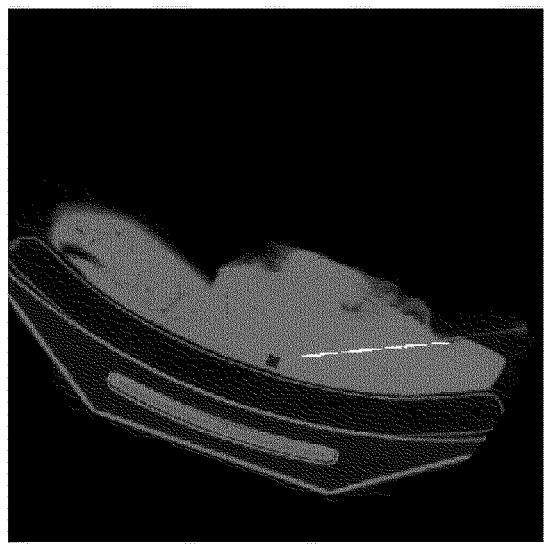
Figure 6A:
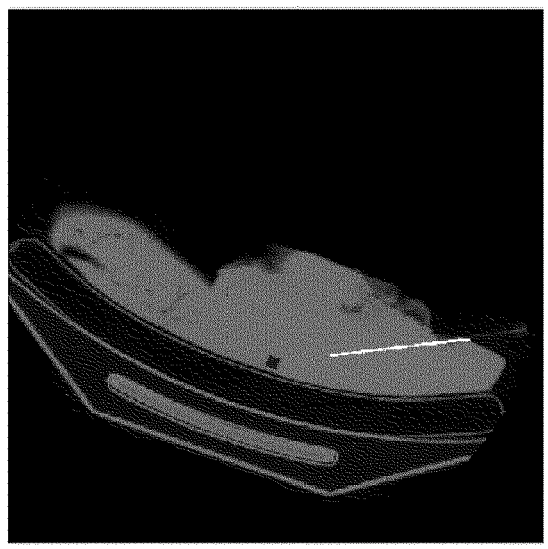

FIGS. 6A-6C show CT images generated as part of an experimental CT fluoroscopy procedure performed on a live pig and illustrating progressive advancement of a needle toward a target, according to inventive concepts of the current disclosure. In one demonstrative and non-limiting experiment, a needle was gradually inserted into an excised pig liver. A series of 12 revolutions were used with gradual advancement of the needle before each revolution. No explicit target was inserted into the liver. However, for simulation purposes, a virtual target (the square in FIGS. 6A-6C) was mathematically defined and superimposed on the needle images to provide an example of how the fluoroscopy mode will proceed. No motion is included in this example. The fluoroscopy process provides a series of 2-D images at 24 images per second (for 2 revolutions per second). The obtained results show that the needle and target object can be viewed from any direction or viewed stereoscopically. In particular, FIGS. 6A-6C represents feedback images corresponding to distinct time instances of the ULD-CTF procedure and they illustrate the real-time advancement of the needle towards the virtual target (the square). For this experiment, projections were separated by 82 of 984 angles, and the dose reduction factor was 82.

Figure 7B:
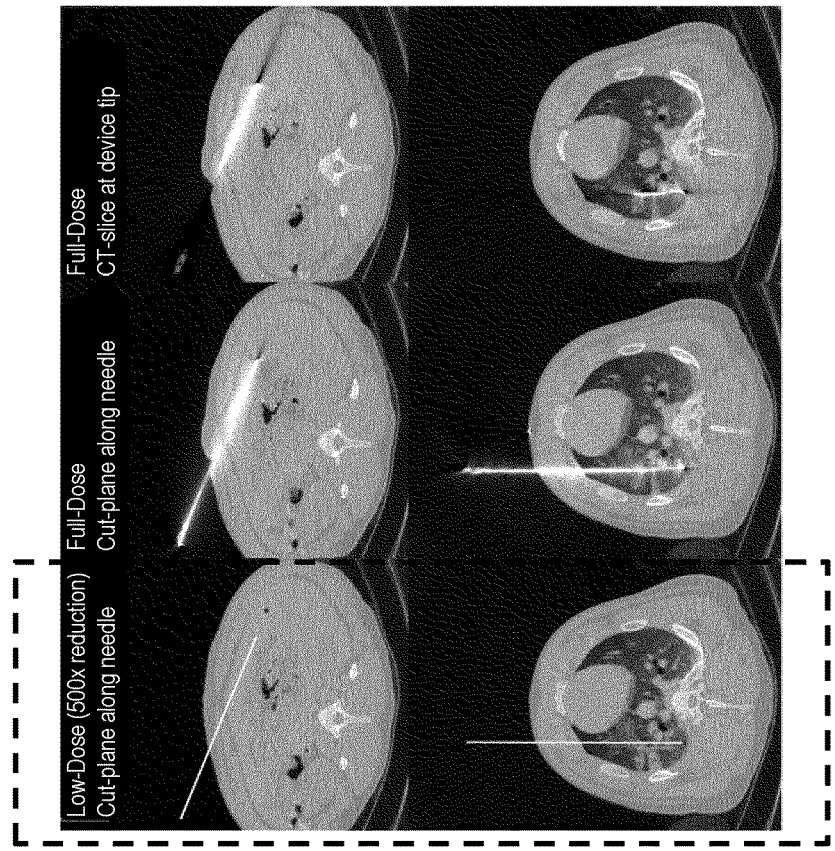
FIGS. 7A and 7B show images illustration experimental results for full dose CCT and ULD-CTF, according to inventive concepts of the current disclosure.
Figure 7A:
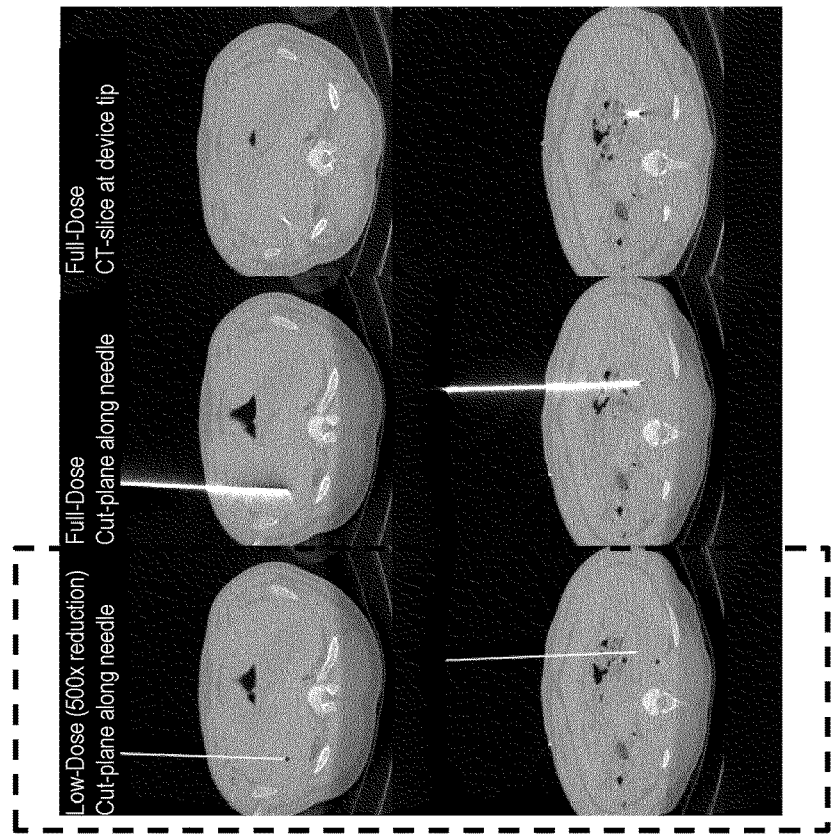

FIGS. 7A and 7B show images illustrating experimental results for full dose CCT and ULD-CTF, according to inventive concepts of the current disclosure. In the experiment, four anatomical sites (lung, kidney, spleen and liver) were imaged using conventional CTF in a series of live pigs. Imaging was performed on a 64-slice CT scanner (HD 750, General Electric, Boston, Mass., USA) with 4 cm axial coverage. Fiducials were placed on the surface of the animal to assist in motion correction. For each anatomical site, a conventional helical scan was performed to define the target volume. Then twelve revolutions were used with needle advancement in between each revolution. The first revolution was performed before insertion of the needle. This was done to allow isolation of the needle via subtraction and cancellation of the fiducials, which can cause artifacts during reconstruction of the needle.

For ULD-CTF, images were generated using just two angles per revolution with an angular separation of 30-90 degrees. This resulted in a dose reduction factor of approximately 984/2=492 since the full dose scans use 984 angles. When two angles are used, the frame rate is equal to the gantry rotation frequency. A visual comparison between the proposed low dose and the conventional full dose reconstruction is shown in FIGS. 7A and 7B for two time frames in the lung. Slices (or view planes) along the needle are shown for the ULD-CTF and full-dose CCT reconstructions on the left and middle columns, respectively. Additionally, a regular CT-slice as it would be displayed by conventional CT scanners is shown on the right. The ULD-CTF images show CT slices along the needle's plane with clear visualization of the needle and the target. However, the CCT images (center columns) show streak artifacts along the needle.

Figure 8:
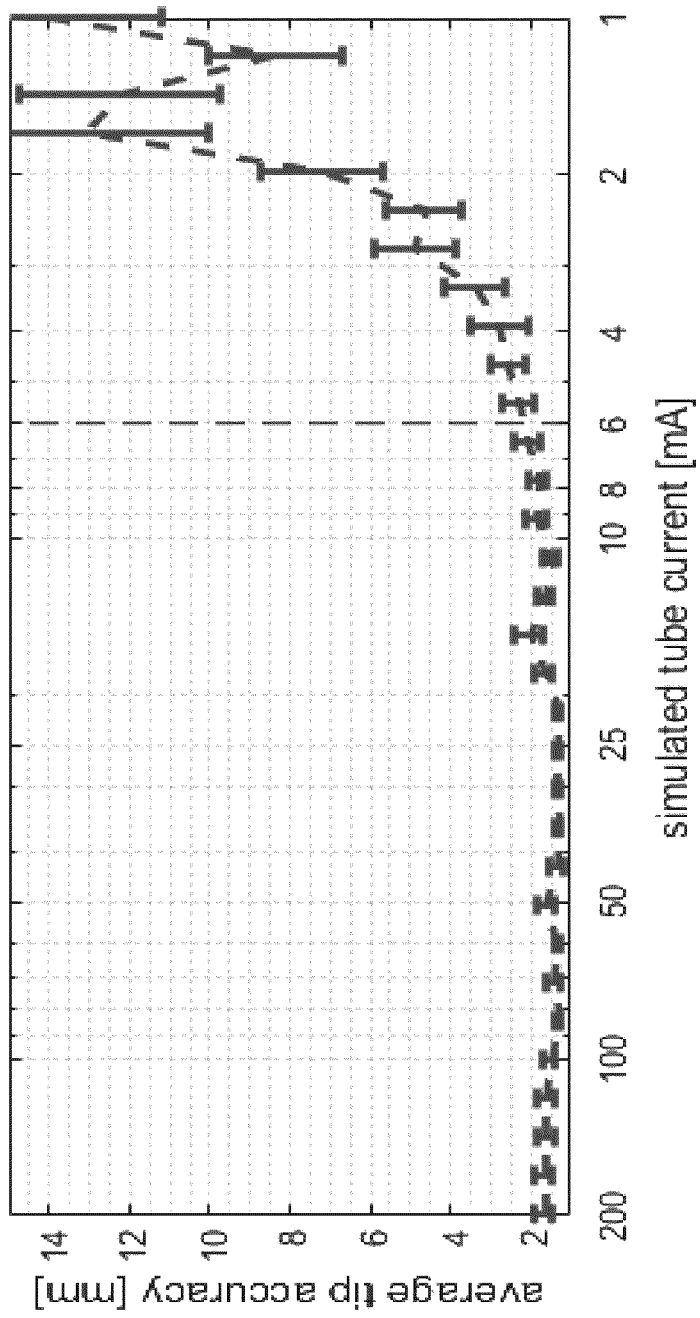
FIG. 8 shows a chart illustrating ULD-CTF reconstruction accuracy as a function of milliamperage.

FIG. 8 shows a chart illustrating ULD-CTF reconstruction accuracy as a function of milliamperage. The ULD-CTF reconstruction accuracy is evaluated in terms of the distance between the needle tip in ULD-CTF reconstructions and corresponding CCT reconstructions Tube currents between 200 mA and 1 mA were simulated by adding artificial noise to image sequences of a pig study acquired at 200 mA in the liver, spleen and kidney. The chart shows the needle tip accuracies for all simulated noise levels. The results show that an average accuracy of 1.58±0.20 mm can be achieved for radiation doses between 200 mA and 6 mA.

Figure 9B:
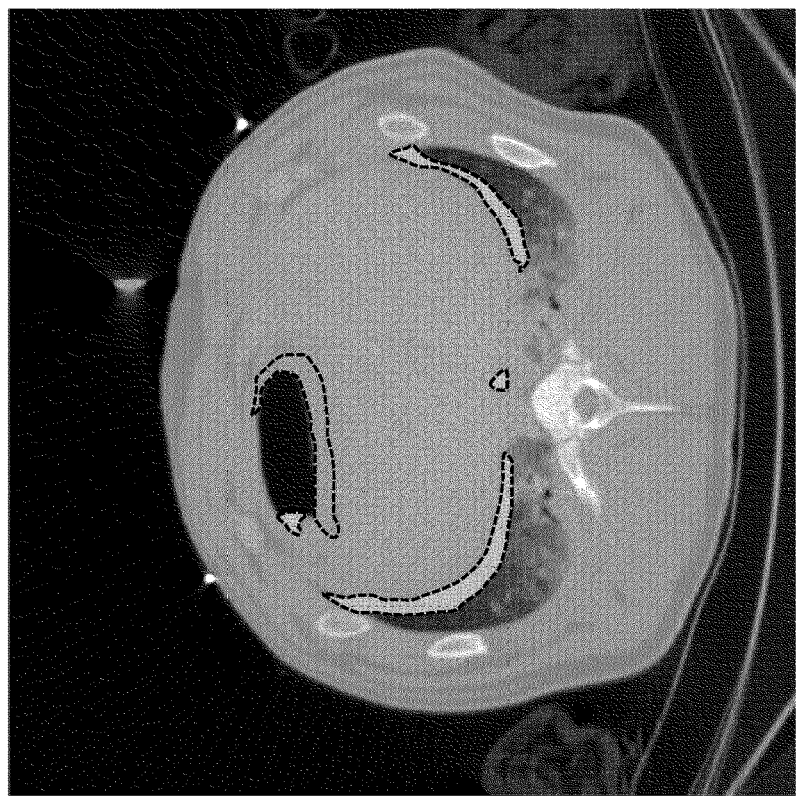
FIGS. 9A and 9B show lung images with different respiratory states.
Figure 9A:
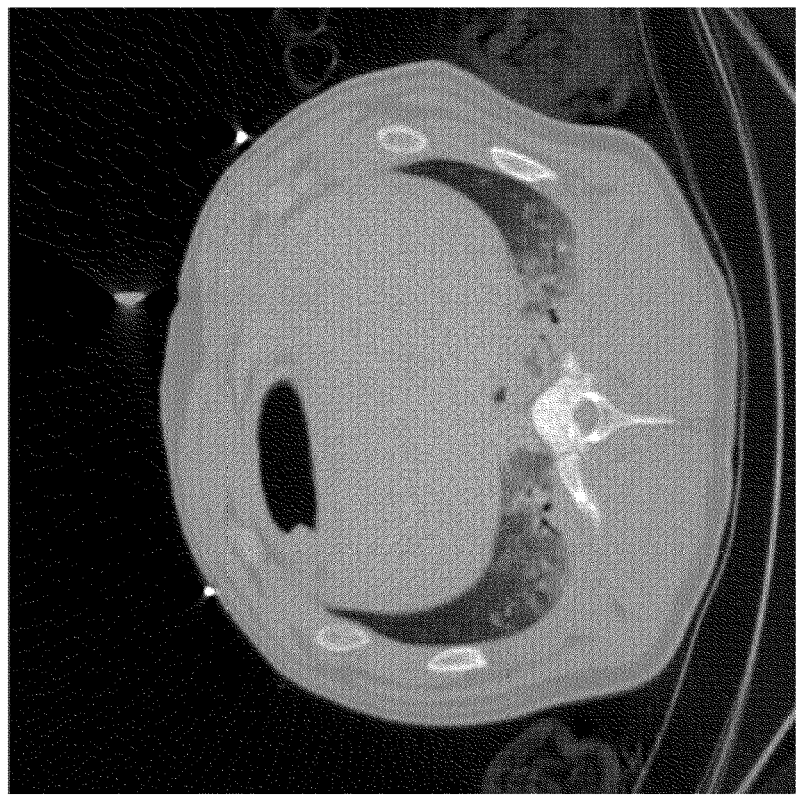

FIGS. 9A and 9B shows images of a lung with different respiratory states. In FIG. 9A, no motion compensation is applied, whereas the image in FIG. 9B is motion compensated. The hashed areas denote registration errors when no motion compensation is applied when reconstructing the feedback images.

The one or more processors 108 can use the plurality of pairs of projections to acquire one or more 2-D or 3-D CT images of the anatomical region and/or the target object (without interrupting the CT fluoroscopy). For instance, the one or more processors 108 can generate one or more additional 2-D or 3-D CT images of the anatomical region and/or the target object using images reconstructed based on the acquired pairs of projections during fluoroscopy (e.g., by eliminating image information indicative of the interventional device). However, since the fluoroscopy process uses fewer projection angles (per unit time or per revolution) as compared to the full dose scan, acquiring a 2-D or 3-D CT images of the target with fewer projection angles per revolution (compared to a full dose scan) can take a longer time to generate.

Figure 10:
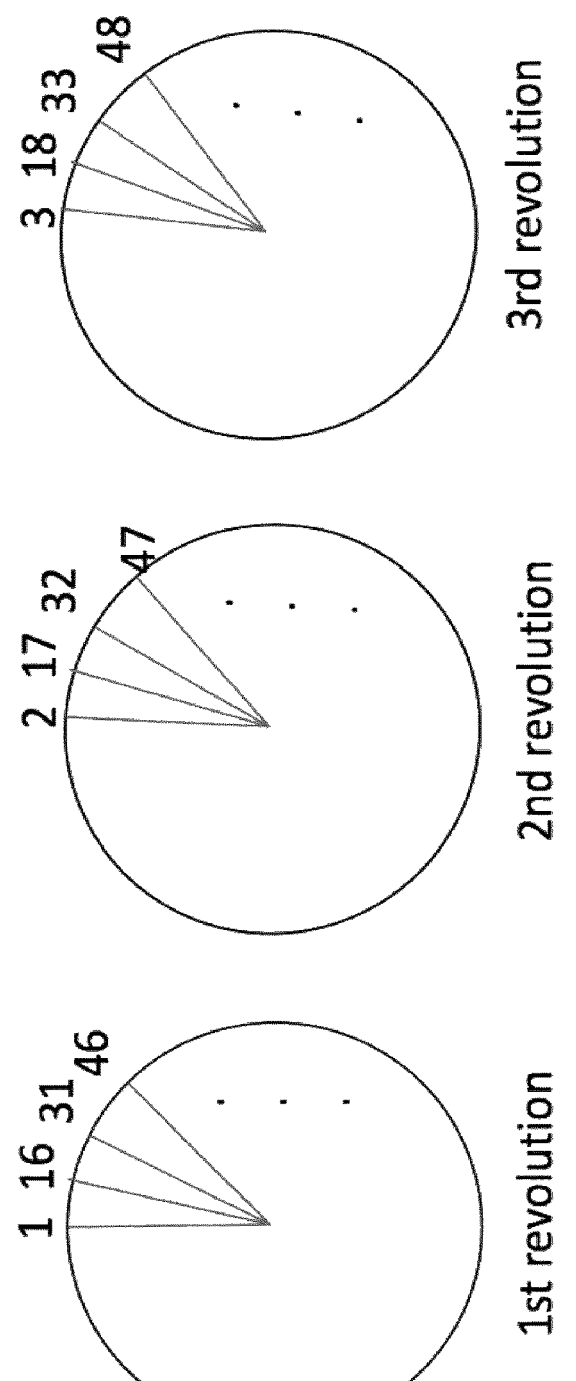
FIG. 10 is a diagram illustrating an example of an interleaved fluoroscopy scan that can be used to generate a CT 3D image of a target object.

FIG. 10 is a diagram illustrating an example of an interleaved fluoroscopy scan that can be used to generate additional 2-D or 3-D CT images of the target object. Suppose that a CT or x-ray scanner acquires interleaved exposures once every 15 angles (as compared to once every single angle for the full dose scan), for example, and advancing one angle per rotation. The dose reduction factor is given by the number of angles skipped between adjacent exposures (in this case 15). A full dose target scan would be acquired every 15 rotations, about 5 seconds assuming a gantry revolution rate of 3/sec. The angle corresponding to 15 projections is 360*15/984=5.5 degrees. In general, the relationship between the separation angle used for interventional device reconstruction is given by angle=360*dose reduction factor/984. Since generating the CT 3D image of the target object involves using a full set of projections (e.g., 984), acquiring such full set of projections takes longer during fluoroscopy than during a full dose scan.

TABLE 1

| dose reduction factor | separation angle | update time |
|---|---|---|
| 10 | 3.65853659 | 3.33333333 |
| 15 | 5.48780488 | 5 |
| 20 | 7.31707317 | 6.66666667 |
| 30 | 10.9756098 | 10 |

Table 1 illustrates the relationship between the dose reduction factor, separation angle, and the update time. The time for a full update of the target image may be given by update time=dose reduction factor/3 for 3 revolutions per second. As the dose reduction factor increases, the update time becomes longer and is probably too long for dose reduction factors greater than twenty. If, for example, a half dose target scan proves acceptable for a certain context, the update times can be cut in half and larger dose reduction factors are possible.

The method 200 can include the one or more processors 108 further acquiring one or more 2-D or 3-D CT images of the target while interrupting the CT fluoroscopy, responsive to detecting a movement of the target that is non-respiratory or greater than a predefined movement threshold. The one or more processors 108 can detect such movement based on a detected movement of the fiducials that exceeds a given threshold value. In response, the one or more processors 108 can prompt the healthcare practitioner to initiate a new set-up (full dose) scan, or can automatically start the new set-up (full dose) scan while informing the healthcare practitioner.

If the one or more processors 108 (or the operator) detect that the only motion that has occurred is respiratory motion, then the target image set (established by eliminating image information indicative of the interventional device) can be used in conjunction with the fiducials to update the target image based on the ongoing fiducial reconstruction. If a non-respiratory shift in the subject's position is detected, the practitioner can interrupt interventional device fluoroscopy, and the CT or x-ray scanner 102 can acquire a new set of target images over a period of perhaps 3-4 seconds after which interventional device fluoroscopy (consistent with the non-respiratory shift) at low dose would resume.

The one or more processors 108 can also improve on the 2-D or 3-D images of the anatomical region and/or the target object, by using signal integration with additional image(s) of the target object. When an additional 2-D or 3-D image of the target object is formed/generated using the ongoing fluoroscopic information (e.g., ULD-CTF projections), the one or more processors 108 can register and/or integrate at least one of the 2-D or 3-D CT images of the target object obtained during setup/full-dose scan, with a newly acquired 2-D or 3-D CT image, to increase the signal-to-noise ratio (SNR) of the 2-D or 3-D images of the target object. In particular, the one or more processors 108 can update (e.g., using weighted averaging) the at least one of the 2-D or 3-D images of the target object obtained during setup, with the newly formed 2-D or 3-D CT image of the target object. The one or more processors 108 can superimpose a corresponding (or newly formed) 2-D or 3-D image of the interventional device, on the updated 2-D or 3-D CT image of the target object, to produce an updated feedback image.

Registration between images can be achieved by the one or more processors 108 using block matching. Block matching can allow detection of motion between corresponding regions/blocks within two images. In some embodiments, if the detected motion(s) is smaller than a given threshold value, the one or more processors 108 can register the images with one another. In other embodiments, the one or more processors 108 use a detected motion (or relative translation or shift) to perform registration. The one or more processors 108 may perform block matching in a limited volume around the target object to increase speed. The one or more processors 108 may also perform the registration by comparing fiducial data to determine which of the target volumes register with each other. For instance, the one or more processors 108 can compare the location of fiducials within two separate images to determine whether the images (or volumes) register with each other. The one or more processors 108 can use any of many possible registration methods.

The fluoroscopy techniques described herein can be implemented with a Siemens dual energy scanner for example. The Siemens dual energy scanner has two sources and detectors separated by a separation angle (e.g., 90 degrees). Although this would easily give two projections separated by 90 degrees, for example, at the same time, a single source CT also can provide two projections separated by 90 degrees in about 0.1 seconds. So there may be no real advantage to having them closer in time. However if the projections were at different energies, tissue intensities could be cancelled making needle segmentation easier. One of the energies could still be used to generate the ongoing unsubtracted target scans.

The Siemens system has an advantage in that the angular separation is large at all dose reduction factors. The dose reduction factor can be decreased by 1.5 because of duplication of exposures by the 90 degree detector.

Figure 11:
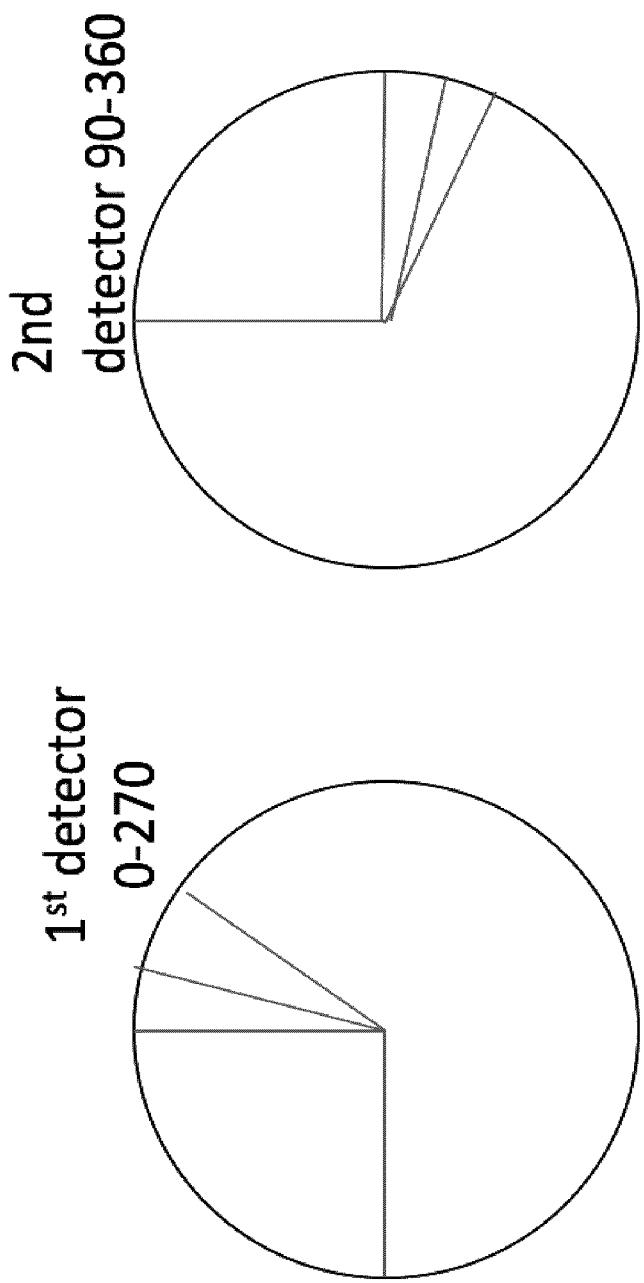
FIG. 11 shows a diagram illustrating an arrangement of two detector-source pairs of a CT scanner.

FIG. 11 shows a diagram illustrating arrangement of two detector-source pairs of CT scanner. The first detector goes from angles values of zero to 270. The second detector goes from 90 to 360 to give a complete data set. The dose reduction factor is still given by the number of angles skipped. The dose can be increased by a factor of 1.5 due to repeated acquisitions by the two detectors at the same angles. Table 2 below shows results illustrating the relationship between the dose reduction factor, separation angle and update time for a proposed Siemens setup.

TABLE 2

| dose reduction factor | separation angle | update time |
|---|---|---|
| 6.7 | 90.0 | 2.2 secs |
| 10.0 | 90.0 | 3.3 |
| 13.3 | 90.0 | 4.4 |
| 20.0 | 90.0 | 6.7 |

Other potential clinical applications of the fluoroscopic techniques described herein can include orthopedic surgery (putting in screws/k-wires, reducing fractures, reducing dislocations, stressing anatomy in real time (e.g., Flexion/extension views, stress views), swallowing evaluation, dynamic pelvic floor evaluation, endoluminal applications such as CT bronchoscopy, colonoscopy, GI tract endoscopy, ERCP, etc., intravascular/intracardiac procedures under CT guidance (locating a catheter in any location in the body in real time), neurosurgery (including real-time neurosurgery under CT guidance such as placement of ventricular shunts), urologic and gynecologic procedures, and/or ear, nose and throat interventions under CT guidance (including sinus procedures, nasal septum operations, and soft tissue interventions).

According to example embodiments, advantages of the ULD-CTF approach can include: 1) markedly improved z-axis coverage (e.g. 4 cm) to visualize interventional devices that would otherwise be "out of plane" during conventional CT fluoroscopy, 2) reconstruction and visualization of the image plane in the interventional device plane so that anatomic objects in the puncture path are always visible, and 3) lack of streak artifact. Because the low dose scans are not reconstructed using conventional filtered back projection, there are no streak artifacts generated by high contrast objects such as needles.

For conventional CTF, interventional device accuracy is primarily limited by slice thickness. Thicker slices are more likely to include the entire interventional device within the scan volume, but volume artifact make precise position of the interventional device within the slice less certain. For ULD-CTF, the accuracy of interventional device localization is not limited by slice thickness, but rather the resolution of the projection data which is governed by image noise. As noise increases at very low mA, there will be a slight degradation in accuracy. However, noise simulations indicate accuracy on the order of 2 mm all the way down to 6 mA. Since CTF is typically performed between 10-100 mA, a 2 mm accuracy appears to be worst possible case. The spatial accuracy of ULD-CTF appears similar or superior to conventional CT fluoroscopy.

Conventional CT fluoroscopy (CTF) is inherently a difficult compromise between interventional device/anatomy visualization and radiation dose. CTF is performed by repeatedly scanning at a single z-axis location during needle advancement towards a target. The only means to reduce radiation dose with CTF are decreasing the number of acquisitions (increasing "blind" needle advancements), decreasing the anatomic coverage in the z-axis (thinner slices increase image noise and increase the probability of the interventional device being out of plane), and decreasing mA (reducing image quality). Each of these radiation reduction steps comes at the price of decreasing the ability to track the interventional device in relation to critical anatomy, thus compromising the core function of CT fluoroscopy.

In the embodiments described in (or contemplated by) the disclosure, a CT scanning system can perform, during a setup phase, a full dose (or setup) CT scan during which a first set of CT projections is acquired, using a conventional number of projection angles per gantry rotation, typically 984, with sufficient dose to delineate a target object (or target region) of interest. A processor associated with the CT scanning system can generate one or more 2-D or 3-D images of an anatomical region including the target object/region. During an ULD-CTF phase when an interventional device is introduced or inserted in the anatomical region, the CT scanning system can acquire a second set of CT projections with the number of acquired projections per gantry rotation being smaller, by a factor of two or more, than the conventional number (e.g., 984) of projection angles used for full dose CT scan. The second set of CT projections may not be necessarily acquired in pairs of CT projections, however, the processor can group (or arrange) the second set of CT projections into pairs, triples, quadruples, or according to subsets of two or more CT projections that are acquired at different projection angles.

The processor can use each subset of CT projections to determine a position of the interventional device within the anatomical region as discussed with regard to FIG. 4. Specifically, the processor can back project a representation of the interventional device (e.g., image region, centerline, or one or more pixels or voxels) in each of the projections in a given subset onto a space volume associated with the anatomical region to determine the position of the interventional device. In general, the processor can use two or more projections when employing back projection to determine the position of the interventional device. The processor can obtain (e.g., reconstruct using the subset of CT projections or use an available) 2-D or 3-D image of the interventional device, and superimpose (or overlay) the 2-D or 3-D image of the interventional device on a 2-D or 3-D image, respectively, of the anatomical region generated using full dose CT scan data to obtain a 2-D or 3-D feedback image or frame, respectively, depicting both the anatomical region with the target region and the interventional device. The processor can generate a separate 2-D or 3-D feedback image or frame for each subset of ULD-CTF projections. The generated 2-D or 3-D feedback images or frames can illustrate the movement of the interventional device over time relative to the target object/region. The processor can display the generated 2-D or 3-D feedback images or frames (or sectional views or other data thereof) to an operator of the interventional device to help for guiding or adjusting movement of the interventional device, for example, toward the target object/region. It is to be appreciated that as use herein, pairs of projections contemplate subsets of two or more projections.

What is claimed is:

1. A method comprising:

generating, using projection data of full dose CT scans at two states of a respiratory cycle of the subject, a pair of two-dimensional (2-D) or three-dimensional (3-D) CT images of an anatomical region of a subject;

simulating, using the pair of 2-D or 3-D CT images of the anatomical region, additional 2-D or 3-D CT images of the anatomical region associated with additional states of the respiratory cycle of the subject, the generated and simulated 2-D or 3-D CT images forming a plurality of 2-D or 3-D CT images of the anatomical region;

acquiring, by rotating a gantry of a CT scanner, a plurality of projection images of an interventional device, penetrating the anatomical region, at a first rate of angular projections per gantry rotation that is at least two times smaller than a second rate of angular projections per gantry rotation used for the full dose CT scans, the plurality of projection images of the interventional device arranged into a plurality of groups of two or more projection images, each group of two or more projection images acquired at a predetermined angular separation;

registering each group of the plurality of groups of two or more projection images, to a corresponding 2-D or 3-D CT image of the anatomical region of the plurality of 2-D or 3-D CT images of the anatomical region;

identifying, for each group of the plurality of groups of two or more projection images, corresponding image regions indicative of the interventional device, each image region indicative of the interventional device in a respective projection image of the group of two or more projection images;

determining, for each group of two or more projection images, a corresponding position and orientation of the interventional device in a 3-D space associated with the anatomical region, using an intersection of representations of the corresponding image regions indicative of the interventional device when back projected into the 3-D space;

superimposing, for each group of two or more projection images, a 2-D or 3-D image of the interventional device on the corresponding 2-D or 3-D CT image of the anatomical region to which the group of two or more projection images is registered, according to the corresponding position and orientation of the interventional device to produce a corresponding 2-D or 3-D output image illustrating a location of the interventional device relative to a target region within the anatomical region at a time of acquisition of the group of projection images; and displaying one or more 2-D or 3-D output images for use to determine a position or to guide movement of the interventional device relative to the target region.

2. The method of claim 1, wherein a full dose CT scan uses a diagnostic dose level to achieve a predetermined signal to noise ratio (SNR) for the 2-D or 3-D CT image of the anatomical region.

3. The method of claim 1, further comprising placing one or more fiducials at a region associated with the anatomical region during the full dose CT scans and when acquiring the plurality of projection images.

4. The method of claim 1, wherein the target region includes at least one of a tumor, a lesion, a musculoskeletal structure, an organ, a duct, or a vessel.

5. The method of claim 1, wherein the pair of 2-D or 3-D CT images of the anatomical region includes a CT angiogram or an image of at least one of: a tumor, a duct, a vessel, a lesion, a musculoskeletal structure, or an organ.

6. The method of claim 1, wherein generating the pair of 2-D or 3-D CT images of the anatomical region includes incorporating at least one of a vascular image of a scanned region, a non-vascular image of the scanned region, or a normal CT image of the scanned region.

7. The method of claim 1, further comprising presenting the one or more 2-D or 3-D output image to a user in a format configured for at least one of: stereoscopic viewing, cross-sectional viewing, fluoroscopic viewing, continuous mode viewing, or user-controlled image transition.

8. The method of claim 1, further comprising presenting the one or more 2-D or 3-D output images to a user to include at least one of: multiple views or CT slices of the one or more 2-D or 3-D output images, a view or a CT slice of the one or more 2-D or 3-D output images along a plane aligned with the interventional device, an indication of a distance relating the interventional device and the target region, an indication of previous positions of the interventional device, or navigational guidance or hint for moving the interventional device.

9. The method of claim 1, further comprising determining positions of one or more fiducials during the respiratory cycle of the subject, using the plurality of 2-D or 3-D CT images of the anatomical region.

10. The method of claim 1, further comprising configuring the acquisition of the plurality of projection images of the interventional device as an acquisition of projections according to a CT scan dose reduction factor, compared to the full dose CT scans, comprising a value from a range of 2 to 492.

11. The method of claim 1, further comprising acquiring the plurality of projection images of the interventional device using two or more x-ray source-detector pairs, the two or more x-ray source-detector pairs simultaneously acquiring, in association with each rotation of the gantry of the CT scanner, a corresponding group of projections of the interventional device.

12. The method of claim 1, wherein the interventional device comprises a needle, wire, probe, catheter, stent, balloon, forceps, an internal anatomic structure, internal orthopedic device, or shunt.

13. The method of claim 1, further comprising forming at least one 2-D or 3-D image of the interventional device using at least one of high pass filtering, image segmentation, thresholding, or subtraction of a first projection associated with the full dose CT scans from a second projection of the interventional device.

14. The method of claim 1, further comprising forming at least one 3D image of the interventional device using a set of time resolved images of the interventional device.

15. The method of claim 1, further comprising selecting, from the plurality of 2-D or 3-D CT images of the anatomical region, the 2-D or 3-D CT image of the anatomical region on which to superimpose the corresponding 2-D or 3-D image of the interventional device, according to one or more positions of one or more fiducials determined during at least part of a respiratory cycle of a subject.

16. The method of claim 1, further comprising acquiring the plurality of projection images of the interventional device while the gantry of the CT scanner is continuously rotated in a same direction.

17. The method of claim 1, wherein projection angles for each gantry rotation are arranged at an offset angle with respect to projection angles for a preceding or subsequent gantry rotation, and the method further comprising acquiring a further one or more 2-D or 3-D CT images of the anatomical region without interrupting the acquisition of the plurality of projection images of the interventional device.

18. The method of claim 1, further comprising increasing a signal to noise ratio (SNR) of the pair 2-D or 3-D CT images of the anatomical region generated using projection data of the full dose CT scans, by registering the 2-D or 3-D CT image of the anatomical region with one or more additional images of the anatomical region.

19. The method of claim 1, further comprising acquiring a further one or more 2-D or 3-D CT images of the anatomical region while interrupting the acquisition of the plurality of projection images of the interventional device, responsive to detecting a movement of the target region that is non-respiratory or greater than a predefined movement threshold.

20. The method of claim 19, further comprising acquiring a second plurality of projection images of the interventional device, in response to the acquisition of the further one or more 2-D or 3-D CT images of the anatomical region.

21. The method of claim 1, further comprising rotating the one or more 2D or 3D output images for 2-D or 3-D visualizations of at least one of the interventional device or the target region.

22. The method of claim 1, further comprising pulsing an x-ray source to acquire the plurality of projection images of the interventional device.

23. The method of claim 1, further comprising acquiring the plurality of projection images of the interventional device within a 50 degree angular rotation of the gantry of the CT scanner.

24. A computed tomography (CT) scanner system, the CT scanner system comprising:
 a rotating gantry including at least one x-ray source-detector pair;
 a processor; and a memory storing computer executable instructions thereon, the computer executable instructions when executed by the processor cause the processor to:

generate, using projection data of full dose CT scans at two states of a respiratory cycle of the subject, a pair of two-dimensional (2-D) or three-dimensional (3-D) CT images of an anatomical region of a subject;

simulate, using the pair of 2-D or 3-D CT images of the anatomical region, additional 2-D or 3-D CT images of the anatomical region associated with additional states of the respiratory cycle of the subject, the generated and simulated 2-D or 3-D CT images forming a plurality of 2-D or 3-D CT images of the anatomical region;

acquire, by rotating the gantry, a plurality of projection images of the interventional device, penetrating an anatomical region of the anatomical region of the subject, at a first rate of angular projections per gantry rotation that is at least two times smaller than a second rate of angular projections per gantry rotation used for the full dose CT scans, the plurality of projection images of the interventional device arranged into a plurality of groups of two or more projection images, each group of two or more projection images acquired at a predetermined angular separation;

register each group of two or more projection images, of the plurality of groups of two or more projection images, to a corresponding 2-D or 3-D CT image of the anatomical region of the plurality of 2-D or 3-D CT images of the anatomical region;

identify, for each group of the plurality of groups of two or more projection images, corresponding image regions indicative of the interventional device, each image region indicative of the interventional device in a respective projection image of the group of two or more projection images;

determine, for each group of two or more projection images, a corresponding position and orientation of the interventional device in a 3-D space associated with the anatomical region, using an intersection of representations of the corresponding image regions indicative of the interventional device when back projected into the 3-D space;

superimpose, for each group of two or more projection images, a corresponding 2-D or 3-D image of the interventional device on the corresponding 2-D or 3-D CT image of the anatomical region to which the group of two or more projection images is registered, according to the corresponding position and orientation of the interventional device to produce a corresponding 2-D or 3-D output image illustrating a location of the interventional device relative to a target region within the anatomical region at a time of acquisition of the group of two or more projection images; and display one or more 2-D or 3-D output images for use to determine a position or to guide movement of the interventional device relative to the target region.

* * * * *